(12) United States Patent
Vendely et al.

(10) Patent No.: US 10,086,116 B2
(45) Date of Patent: Oct. 2, 2018

(54) ADJUNCT MATERIAL TO PROVIDE CONTROLLED DRUG RELEASE

(71) Applicant: Ethicon Endo-Surgery, LLC, Guaynabo, PR (US)

(72) Inventors: Michael J. Vendely, Lebanon, OH (US); Chad E. Eckert, Milford, OH (US); Frederick E. Shelton, IV, Hillsboro, OH (US); Jason L. Harris, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 416 days.

(21) Appl. No.: 14/840,716

(22) Filed: Aug. 31, 2015

(65) Prior Publication Data
US 2017/0056569 A1 Mar. 2, 2017

(51) Int. Cl.
| | |
|---|---|
| A61L 31/16 | (2006.01) |
| A61L 27/18 | (2006.01) |
| A61L 27/34 | (2006.01) |
| A61L 27/54 | (2006.01) |
| A61L 27/56 | (2006.01) |
| A61L 27/58 | (2006.01) |
| A61B 17/072 | (2006.01) |
| A61L 31/04 | (2006.01) |

(Continued)

(52) U.S. Cl.
CPC ........ *A61L 31/16* (2013.01); *A61B 17/07207* (2013.01); *A61B 17/07292* (2013.01); *A61L 27/18* (2013.01); *A61L 27/34* (2013.01); *A61L 27/54* (2013.01); *A61L 27/56* (2013.01); *A61L 27/58* (2013.01); *A61L 31/04* (2013.01); *A61L 31/148* (2013.01); *A61B 2017/00893* (2013.01); *A61B 2017/07271* (2013.01); *A61B 2017/07285* (2013.01); *A61L 2430/34* (2013.01)

(58) Field of Classification Search
CPC .. A61L 31/16; A61B 17/07207; A61B 17/072
USPC ............. 227/176.1, 175.1, 178.1, 180.1
See application file for complete search history.

(56) References Cited

U.S. PATENT DOCUMENTS

| | | | | |
|---|---|---|---|---|
| 4,024,871 A | * | 5/1977 | Stephenson | A61L 17/005 424/443 |
| 5,123,912 A | | 6/1992 | Kaplan et al. | |

(Continued)

FOREIGN PATENT DOCUMENTS

| | | |
|---|---|---|
| EP | 0 640 315 A1 | 3/1995 |
| WO | WO-2010/109021 A2 | 9/2010 |

OTHER PUBLICATIONS

U.S. Appl. No. 14/840,613 entitled, "Medicant Eluting Adjuncts and Methods of Using Medicant Eluting Adjuncts" filed Aug. 31, 2015:1-202.

(Continued)

*Primary Examiner* — Nathaniel Chukwurah
(74) *Attorney, Agent, or Firm* — Mintz Levin Cohn Ferris Glovsky and Popeo, P.C.

(57) ABSTRACT

Adjunct material retained by a staple cartridge assembly is provided. The adjunct material provides elution of medicants therefrom such that release of one medicant regulates release of another medicant. A first medicant is released as a bolus dose substantially immediately upon delivery of the adjunct material to tissue. The second medicant is associated with the staple cartridge assembly in a manner such that release of the second medicant to tissue is regulated by the release of the first medicant.

20 Claims, 19 Drawing Sheets

(51) Int. Cl.
*A61L 31/14* (2006.01)
*A61B 17/00* (2006.01)

(56) References Cited

U.S. PATENT DOCUMENTS

| | | | |
|---|---|---|---|
| 5,282,829 A | 2/1994 | Hermes | |
| 5,395,033 A | 3/1995 | Byrne et al. | |
| 5,446,108 A | 8/1995 | Jiang | |
| 5,533,521 A | 7/1996 | Granger | |
| 5,776,130 A | 7/1998 | Buysse et al. | |
| 5,814,057 A | 9/1998 | Oi et al. | |
| 5,836,970 A | 11/1998 | Pandit | |
| 5,980,518 A | 11/1999 | Carr et al. | |
| 6,241,139 B1* | 6/2001 | Milliman | A61B 17/07207 227/175.1 |
| 6,551,353 B1* | 4/2003 | Baker | A61K 9/0092 425/373 |
| 6,620,166 B1 | 9/2003 | Wenstrom, Jr. et al. | |
| 6,716,233 B1 | 4/2004 | Whitman | |
| 6,821,273 B2 | 11/2004 | Mollenauer | |
| 7,143,925 B2 | 12/2006 | Shelton, IV et al. | |
| 7,160,299 B2 | 1/2007 | Baily | |
| 7,238,195 B2 | 7/2007 | Viola | |
| 7,316,693 B2 | 1/2008 | Viola | |
| 7,464,847 B2 | 12/2008 | Viola et al. | |
| 7,550,152 B2 | 6/2009 | Pandit et al. | |
| 7,559,453 B2 | 7/2009 | Heinrich et al. | |
| 7,601,118 B2 | 10/2009 | Smith et al. | |
| 7,607,557 B2 | 10/2009 | Shelton, IV et al. | |
| 7,708,180 B2 | 5/2010 | Murray et al. | |
| 7,794,475 B2 | 9/2010 | Hess et al. | |
| 7,845,533 B2 | 12/2010 | Marczyk et al. | |
| 8,097,017 B2* | 1/2012 | Viola | A61B 17/064 606/215 |
| 8,215,531 B2 | 7/2012 | Shelton, IV et al. | |
| 8,273,369 B2 | 9/2012 | Moloye-Olabisi et al. | |
| 8,317,070 B2 | 11/2012 | Hueil et al. | |
| 8,319,211 B2 | 11/2012 | Sakuma et al. | |
| 8,329,211 B2 | 12/2012 | Moloye-Olabisi et al. | |
| 8,383,147 B2 | 2/2013 | Shetty et al. | |
| 8,393,514 B2 | 3/2013 | Shelton, IV et al. | |
| 8,464,925 B2 | 6/2013 | Hull et al. | |
| 8,486,155 B2 | 7/2013 | McAlister et al. | |
| 8,652,506 B2 | 2/2014 | Sikes et al. | |
| 8,663,277 B2 | 3/2014 | Collier et al. | |
| 2004/0254608 A1* | 12/2004 | Huitema | A61B 17/0644 606/219 |
| 2005/0119723 A1* | 6/2005 | Peacock, III | A61L 31/12 623/1.15 |
| 2005/0131390 A1 | 6/2005 | Heinrich et al. | |
| 2005/0208100 A1* | 9/2005 | Weber | A61L 27/34 424/426 |
| 2006/0173470 A1* | 8/2006 | Oray | A61B 17/07207 606/151 |
| 2006/0235469 A1 | 10/2006 | Viola | |
| 2007/0112414 A1 | 5/2007 | Parker et al. | |
| 2007/0123781 A1 | 5/2007 | Callahan et al. | |
| 2007/0134292 A1 | 6/2007 | Suokas et al. | |
| 2007/0173787 A1 | 7/2007 | Huang et al. | |
| 2008/0110961 A1 | 5/2008 | Voegele et al. | |
| 2008/0114381 A1 | 5/2008 | Voegele et al. | |
| 2009/0001122 A1* | 1/2009 | Prommersberger | A61B 17/07207 227/176.1 |
| 2009/0024144 A1 | 1/2009 | Zeiner et al. | |
| 2009/0062799 A1 | 3/2009 | Holsten et al. | |
| 2009/0104640 A1 | 4/2009 | Barron et al. | |
| 2010/0036379 A1 | 2/2010 | Prakash et al. | |
| 2010/0087840 A1* | 4/2010 | Ebersole | A61B 17/07207 606/151 |
| 2010/0131050 A1* | 5/2010 | Zhao | A61L 31/022 623/1.42 |
| 2010/0137990 A1 | 6/2010 | Apatsidis et al. | |
| 2010/0179545 A1 | 7/2010 | Twomey et al. | |
| 2010/0312146 A1 | 12/2010 | Holsten | |
| 2011/0066168 A1 | 3/2011 | Magnusson et al. | |
| 2012/0241497 A1* | 9/2012 | Mandakolathur Vasudevan | A61B 17/00491 227/176.1 |
| 2012/0241505 A1 | 9/2012 | Alexander, III et al. | |
| 2012/0312860 A1 | 12/2012 | Ming et al. | |
| 2012/0318842 A1 | 12/2012 | Anim et al. | |
| 2013/0146643 A1 | 6/2013 | Schmid et al. | |
| 2013/0149343 A1 | 6/2013 | Pesnell et al. | |
| 2013/0221065 A1 | 8/2013 | Aronhalt et al. | |
| 2013/0256365 A1 | 10/2013 | Shelton, IV et al. | |
| 2013/0256367 A1 | 10/2013 | Scheib et al. | |
| 2013/0256377 A1 | 10/2013 | Schmid et al. | |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0272575 A1 | 10/2015 | Leimbach et al. | |

OTHER PUBLICATIONS

U.S. Appl. No. 14/840,613 entitled, "Medicant Eluting Adjuncts and Methods of Using Medicant Eluting Adjuncts" filed Aug. 31, 2015:203-301.
U.S. Appl. No. 14/840,255 entitled "Adjunct Material to Promote Tissue Growth" filed Aug. 31, 2015.
U.S. Appl. No. 14/840,527 entitled "Composite Adjunct Materials for Delivering Medicants" filed Aug. 31, 2015.
U.S. Appl. No. 14/840,659 entitled "Adjunct Material to Provide Heterogeneous Drug Elution" filed Aug. 31, 2015.
U.S. Appl. No. 14/840,386 entitled "Surgical Adjuncts Having Medicants Controllably Releasable Therefrom" filed Aug. 31, 2015.
U.S. Appl. No. 14/840,406 entitled "Matrix Metalloproteinase Inhibiting Adjuncts for Surgical Devices" filed Aug. 31, 2015.
U.S. Appl. No. 14/841,139 entitled "Adjunct Material to Provide Controlled Drug Elution" filed Aug. 31, 2015.
U.S. Appl. No. 14/840,431 entitled "Surgical Adjuncts With Medicants Affected by Activator Materials" filed Aug. 31, 2015.
U.S. Appl. No. 14/840,523 entitled "Adjuncts for Surgical Devices Including Agonists and Antagonists" filed Aug. 31, 2015.
U.S. Appl. No. 14/498,145 entitled "Method for Creating a Staple Line" filed Sep. 26, 2014.
U.S. Appl. No. 14/667,842 entitled "Method of Applying a Buttress to a Surgical Stapler" filed Mar. 25, 2015.
U.S. Appl. No. 14/300,954, entitled "Adjunct Materials and Methods of Using Same in Surgical Methods for Tissue Sealing," filed Jun. 10, 2014.
U.S. Appl. No. 14/318,996 entitled "Fastener Cartridges Including Extensions Having Different Configurations" filed Jun. 30, 2014.
U.S. Appl. No. 14/667,874 entitled "Malleable Bioabsorbable Polymer Adhesive for Releasably Attaching a Staple Buttress to a Surgical Stapler" filed Mar. 25, 2015.
U.S. Appl. No. 14/840,589 entitled "Adjunct Material to Provide Drug Elution from Vessels" filed Aug. 31, 2015.
U.S. Appl. No. 14/840,758 entitled "Surgical Adjuncts With Medicants Affected by Activators" filed Aug. 31, 2015.
U.S. Appl. No. 14/840,878 entitled "Surgical Adjuncts and Medicants for Promoting Lung Function" filed Aug. 31, 2015.
U.S. Appl. No. 14/840,927 entitled "Adjunct Material to Promote Tissue Growth in a Colon" filed Aug. 31, 2015.
U.S. Appl. No. 14/841,060 entitled, "Tubular Surgical Constructs Including Adjunct Material" filed Aug. 31, 2015.
U.S. Appl. No. 14/841,074 entitled "Adjunct Material for Delivery to Stomach Tissue" filed Aug. 31, 2015.
U.S. Appl. No. 14/841,147 entitled "Inducing Tissue Adhesions Using Surgical Adjuncts and Medicants" filed Aug. 31, 2015.
U.S. Appl. No. 14/841,180 entitled "Adjunct Material for Delivery to Live Tissue" filed Aug. 31, 2015.
U.S. Appl. No. 14/841,115 entitled "Adjunct Material for Delivery to Colon Tissue" filed Aug. 31, 2015.

(56) References Cited

OTHER PUBLICATIONS

Abbas, Anastomotic leak: should we continue to accept the risks? Dis Colon Rectum. Jun. 2010;53(6):859-60.
Achneck et al., A comprehensive review of topical hemostatic agents. Ann Surg 2010; 251:217-228.
Adas et al., Mesenchymal stem cells improve the healing of ischemic colonic anastomoses (experimental study). Langenbecks Arch Surg. Jan. 2011;396(1):115-26.
Agren et al., Action of matrix metalloproteinases at restricted sites in colon anastomosis repair: an immunohistochemical and biochemical study. Surgery. Jul. 2006;140(1):72-82.
Al Jabri et al., Management and prevention of pelvic adhesions. Sem Rep Med 2011; 29(2):130-137.
Anegg et al., Efficiency of fleece-bound sealing (TachoSil) of air leaks in lung surgery: a prospective randomised trial. Eur J Cardiothoracic Surg 2007; 31(2):198-202.
Armstrong et al., The effect of three hemostatic agents on early bone healing in an animal model. BMC Surgery 2010; 10:37.
Arnold et al., A comparison of burst pressure between buttressed versus non-buttressed staple-lines in an animal model. Obes Surg. Feb. 2005;15(2):164-71.
Assalia et al., Staple-line reinforcement with bovine pericardium in laparoscopic sleeve gastrectomy: experimental comparative study in pigs. Obes Surg. Feb. 2007;17(2):222-8.
Astafiev GV [All State Laboratory for Surgery Research]. Investigation of processes relating to tissue compression in suturing and stapling apparatus. Surgical Staplers (Chirurgicheskiey Shivayushiye Apparaty). 1967;7.
Attard et al., The effects of systemic hypoxia on colon anastomotic healing: an animal model. Dis Colon Rectum. Jul. 2005;48(7):1460-70.
Aydin et al., FACS, Bariatric Times. 2010;7(3):8-13.
Baca et al., Icodextrin and Seprafilm® do not interfere with colonic anastomosis in rats. Eur Surg Res 2007; 39:318-323.
Baker et al. The science of stapling and leaks. Obes Surg. 2004;14:1290-1298.
Bartczak et al., Manipulation of in vitro angiogenesis using peptide-coated gold nanoparticles. ACS Nano. Jun. 25, 2013;7(6):5628-36.
Belda-Sanchis et al., Surgical sealant for preventing air leaks after pulmonary resections in patients with lung cancer. Cochrane Database Syst Rev 2005; 3:CD003051.
Bezwada, Controlled Release of Drugs from Novel Absorbable Oligomers and Polymers, White Paper, Bezwada Biomedical, 2008.
Bezwada, Functionalized Triclosan for Controlled Release Applications. White Paper, Bezwada Biomedical. 2008.
Bezwada, Nitric Oxide and Drug Releasing Hydrolysable Macromers, Oligomers and Polymers, Ch. 11 of Biomaterials, ACS Symposium Series; American Chemical Society: Washington, DC, 2010.
Bezwada, Nitric Oxide and Drug Releasing Hydrolysable Macromers, Oligomers and Polymers. White Paper, Bezwada Biomedical. 2009.
Bischoff et al., A rheological network model for the continuum anisotropic and viscoelastic behavior of soft tissue. Biomech Model Mechanobiol. Sep. 2004;3(1):56-65.
Bischoff, Reduced parameter formulation for incorporating fiber level viscoelasticity into tissue level biomechanical models. Ann Biomed Eng. Jul. 2006;34(7):1164-72.
Blouhos et al., The integrity of colonic anastomoses following the intraperitoneal administration of oxaliplatin. Int J Colorectal Dis 2010; 25(7): 835-841.
Brady et al., Use of autologous platelet gel in bariatric surgery. Journal of Extra-Corporeal Technology 2006; 38(2):161-164.
Broughton G 2nd, Janis JE, Attinger CE. The basic science of wound healing. Plast Reconstr Surg. Jun. 2006;117(7 Suppl):12S-34S.
Callery et al., Collagen matrix staple line reinforcement in gastric bypass. Surg Obes Rel Dis 2010. Article in press.
D'Andrilli et al., A prospective randomized study to assess the efficacy of a surgical sealant to treat air leaks in lung surgery. Eur J Cardiothoracic Surg 2009; 35:817-821.
DeCamp et al., Patient and surgical factors influencing air leak after lung volume reduction surgery: lessons learned from the National Emphysema Treatment Trial. Ann Thorac Surg. Jul. 2006;82(1):197-206.
Deshaies et al., Antiangiogenic agents and late anastomotic complications. J Surg Onc 2010; 101(2):180-183.
Dubay et al., Acute wound healing: the biology of acute wound failure. Surg Clin North Am. Jun. 2003;83(3):463-81.
Dujovny et al., Minimum vascular occlusive force. J Neurosurg. Nov. 1979;51(5):662-8.
Efthimiou et al., Fibrin sealant associated with increased body temperature and leukocytosis after laparoscopic gastric bypass. Surg Obes Rel Dis 2010; 6:46-49.
Elariny et al., Tissue thickness of human stomach measured on excised gastric specimens of obese patients. Surg Technol Int. XIV (2005); 14:119-124.
Enestvedt et al., Clinical review: Healing in gastrointestinal anastomoses, part II. Microsurgery. 2006;26(3):137-43.
Ersoy et al., Effects of oxaliplatin and 5-Fluorouracil on the healing of colon anastomoses. Surg Today 2009; 39:38-43.
Fedakar-Senyucel et al., The effects of local and sustained release of fibroblast growth factor on wound healing in esophageal anastomoses. J. Ped Surg 2008; 43 (2):290-295.
Fingerhut et al., Use of sealants in pancreatic surgery: Critical appraisal of the literature. Dig Surg 2009; 26:7-14.
Frank et al., Clamping the small intestineduring surgery: predicted and measured sealing forces. Proc Inst Mech Eng H. 1995;209(2):111-5.
Fullum et al., Decreasing anastomotic and staple line leaks after laparoscopic Roux-en-Y gastric bypass. Surg Endosc 2009; 23(6):1403-1408.
Goto et al., Evaluation of the mechanical strength and patency of functional end-to-end anastomoses. Surg Endosc. Sep. 2007;21(9):1508-11.
Gregersen et al., Biomechanics of the gastrointestinal tract. Neurogastroenterol Motil. Dec. 1996;8(4):277-97.
Gu et al., Effects of hydration and fixed charge density on fluid transport in charged hydrated soft tissues. Ann Biomed Eng. Nov. 2003;31(10)1162-70.
Hardy KJ. Non-suture anastomosis: the historical development. Aust N Z J Surg. Aug. 1990;60(8):625-33.
Hendriks et al., Healing of experimental intestinal anastomoses. Parameters for repair. Dis Colon Rectum. Oct. 1990;33(10):891-901.
Huh et al., Anastomotic leakage after laparoscopic resection of rectal cancer: The impact of fibrin glue. Am J Surg 2010; 1991(4):435-441.
Jönsson et al., Breaking strength of small intestinal anastomoses. Am J Surg. Jun. 1983;145(6):800-3.
Kaemmer et al., Erythropoietin (EPO) influences colonic anastomotic healing in a rat model by modulating collagen metabolism. J Surg Res. Oct. 2010;163(2):e67-72.
Kanellos et al., Healing of colonic anastomoses after immediate postoperative intraperitoneal administration of oxaliplatin. Int J Colorectal Dis 2008; 23(12):1185-1191.
Kennelly et al., Electrical field stimulation promotes anastomotic healing in poorly perfused rat colon. Int J Colorectal Dis 2011; 26:339-344.
Kirfel et al., Impaired intestinal wound healing in Fhl2-deficient mice is due to disturbed collagen metabolism. Exp Cell Res. Dec. 10, 2008;314(20):3684-91.
Kjaergard HK. Suture support: is it advantageous? Am J Surg. Aug. 2001;182(2 Suppl): 15S-20S.
Klein et al., Physiology and pathophysiology of matrix metalloproteases. Amino Acids. Springer, Jul. 18, 2010.
Lang et al., Efficacy and safety of topical application of human fibrinogen/thrombin-coated collagen patch (TachoComb) for treatment of air leakage afgter standard lobectomy. Eur J Cardiothorac Surg 2004; 25:160-166.
Lee et al., Efficacy of posterior fixation suture augmented with talc or doxycycline. Graefe's Archive for Clinical and Experimental Ophthalmology 2010; 248(9):1287-1292.

(56) References Cited

OTHER PUBLICATIONS

Lee et al., Using Surgicel to buttress the staple line in lung volume reduction surgery for chronic obstructive pulmonary disease. J Thorac Card Surg 2006; 131(2):495-496.

Letowska-Andrzejewicz et al., The use of morphometric and fractal parameters to assess the effects of 5-fluorouracil, interferon and dexamethasone treatment on colonic anastomosis healing: An experimental study in rats. Folia Histochemica et Cytobiologica 2011; 49(1):80-89.

Li et al., Combination of fibrin glue with growth hormone augments healing of incomplete intestinal anastomoses in a rat model of intra-abdominal sepsis: a dynamic study. J Invest Surg. Sep.-Oct. 2007;20(5):301-6.

Li et al., Effect of the combination of fibrin glue and growth hormone on incomplete intestinal anastomoses in a rat model of intra-abdominal sepsis. J Surg Res 2006; 131(1):1110117.

Malapert et al., Surgical sealant for the prevention of prolonged air leak after lung resection: Meta-analysis. Ann Thor Surg 2010; 90(6):1779-1785.

Martens et al., Postoperative changes in collagen synthesis in between small and large bowel. intestinal anastomoses of the rat: differences Gut 1991;32;1482-1487.

McGuire et al., An in vitro assessment of tissue compression damage during circular stapler approximation tests, measuring expulsion of intracellular fluid and force. Proc Inst Mech Eng [H]. 2001;215(6):589-597.

Menzies et al., Use of icodextrin 4% solution in the prevention of adhesion formation following general surgery: From the multicentre ARIEL Registry. Ann Royal Coll Surg 2006; 88(4):375-382.

Mongardini et al., [The use of Floseal in the prevention and treatment of intra- and post-operative hemorrhage in the surgical treatment of hemorrhoids and colporectocele. Preliminary results]. G Chir. Oct. 2003;24(10):377-81. Italian.

Munireddy et al., Intra-abdominal healing: gastrointestinal tract and adhesions. Surg Clin North Am. Dec. 2010;90(6):1227-36.

Nandakumar et al., Anastomoses of the lower gastrointestinal tract. Nat Rev Gastroenterol Hepatol. Dec. 2009;6(12):709-16.

Nandakumar et al., Surgical adhesive increases burst pressure and seals leaks in stapled gastrojejunostomy. Surg Obes Rel Dis 2010; 6:498-502.

Nguyen et al., The efficacy of fibrin sealant in prevention of anastomotic leak after laparoscopic gastric bypass. J Surg Res 2004; 122:218-224.

Nomori et al., Gelatin-resorcinol-formaldehyde-glutaraldehyde glue-spread stapler prevents air leakage from the lung. Ann Thorac Surg 1997; 63(2):352-355.

Nomori et al., The efficacy and side effects of gelatin-resorcinol formaldehyde-glutaraldehyde (GRFG) glue for preventing and sealing pulmonary air leakage. Surgery Today 2000; 30(3):244-248.

Oz et al., Preliminary experience with laser reinforcement of vascular anastomoses. Proceedings of SPIE—The International Society for Optimal Engineering 1991; 1422:147-150.

Ozel et al., Effect of early preoperative 5-fluorouracil on the integrity of colonic anastomoses in rats. World J Gastroenterology 2009; 15(33):4156-4162.

Pascual et al., Adipose-derived mesenchymal stem cells in biosutures do not improve healing of experimental colonic anastomoses. Br J Surg 2008; 95(9)1180-1184.

Pascual et al., Biosutures improve healing of experimental weak colonic anastomoses. Int J Colorectal Dis 2010; 25(12):1447-1451.

Pasternak et al., Doxycycline-coated sutures improve mechanical strength of intestinal anastomoses. Int J Colorectal Dis 2008; 23(3):271-276.

Pavlidis et al., The effect of bevacizumab on colon anastomotic healing in rats. Int J Colorectal Dis 2010; 25(12):1465-1473.

Rena et al., Air-leak management after upper lobectomy in patients with fused fissure and chronic obstructive pulmonary disease: A pilot trial comparing sealant and standard treatment. Int Cardiovasc Thor Surg 2009; 9(6):973-977.

Rijcken et al., Insulin-like growth factor 1-coated sutures improve anastomotic healing in an experimental model of colitis. Br J Surg 2010; 97(2): 258-265.

Robson et al., Wound healing: biologic features and approaches to maximize healing trajectories. Curr Probl Surg. Feb. 2001;38(2):72-140.

Rusca et al., Everting versus inverting gastrointestinal anastomoses: bacterial leakage and anastomotic disruption. Ann Surg. May 1969;169(5):727-35.

Sakallioglu et al., Sustained local application of low-dose epidermal growth factor on steroid-inhibited colonic wound healing. J Ped Surg 2004; 39(4):591-595.

Sanbeyoulu et al., Does becaplermin (platelet-derived growth factor-BB) reverse detrimental effects of ischemia on colonic anastomosis? Dis Col Rect 2003; 46(4):516-520.

Schnriger et al., Prevention of postoperative peritoneal adhesions: A review of the literature. Am J Surg 2011; 201(1):111-121.

Seyda, "Stem Cells and Tissue Engineering" PowerPoint Presentation, Aug. 18, 2009.

Shogan et al., Collagen degradation and MMP9 activation by Enterococcus faecalis contribute to intestinal anastomotic leak. Sci Transl Med. May 6, 2015;7(286):286ra68.

Siemonsma et al., Doxycycline improves wound strength after intestinal anastomosis in the rat. Surgery. Mar. 2003;133(3):268-76.

Sileshi et al., Application of energy-based technologies and topical hemostatic agents in the management of surgical hemostasis. Vascular 2010; 18(4):197-204.

Spector et al., Comparison of hemostatic properties between collagen and synthetic buttress materials used in staple line reinforcement in a swine splenic hemorrhage model. Surg Endosc 2011; 25(4):1148-1152.

Spector et al., In vitro large diameter bowel anastomosis using a temperature controlled laser tissue soldering system and albumin stent. Lasers in Surgery and Medicine 2009; 41(7):504-508.

Stammberger et al., Buttressing the staple line in lung volume reduction surgery: a randomized three-center study. Ann Thorac Surg. Dec. 2000;70(6):1820-5.

Subhas et al., Topical gentamicin does not provide any additional anastomotic strength when combined with fibrin glue. Am J Surg 2001; 201 (3):339-343.

Suresh et al., Seprafilm slurry does not increase complication rates after laparoscopic colectomy. Surg Endosc. Aug. 2011;25(8):2661-5.

Syk et al., Inhibition of matrix metalloproteinases enhances breaking strength of colonic anastomoses in an experimental model. Br J Surg. Feb. 2001;88(2):228-34.

Thompson et al., Clinical review: Healing in gastrointestinal anastomoses, part I. Microsurgery. 2006;26(3):131-6.

Uludag et al., Covering the colon anastomoses with amniotic membrane prevents the negative effects of early intraperitoneal 5-FU administration on anastomotic healing. Int J Colorectal Dis 2010; 25(2):223-232.

Uludag et al., Effects of amniotic membrane on the healing of normal and high-risk colonic anastomoses in rats. Int J Colorectal Dis 2009; 24:809-817.

Uludag et al., Effects of amniotic membrane on the healing of primary colonic anastomoses in the cecal ligation and puncture model of secondary peritonitis in rats. Int J Colorectal Dis 2009; 24(5):559-567.

Uludag et al., Effects of the amniotic membrane on healing of colonic anastomoses in experimental left-sided colonic obstruction. Langebeck's Arch Surg 2010; 395(5):535-543.

van der Stappen et al., Collagenolytic activity in experimental intestinal anastomoses. Differences between small and large bowel and evidence for the presence of collagenase. Int J Colorectal Dis. Jun. 1992;7(2):95-101.

Wang et al., Effect of the combination of fibrin glue and growth hormone on intestinal anastomoses in a pig model of traumatic shock associated with peritonitis. Work J Surg 2009; 33(3):567-576.

Witte et al., Repair of full-thickness bowel injury. Crit Care Med. Aug. 2003;31(8 Suppl):S538-46.

(56) References Cited

OTHER PUBLICATIONS

Yo et al., Buttressing of the staple line in gastrointestinal anastomoses: overview of new technology designed to reduce perioperative complications. Dig Surg. 2006;23(5-6):283-91.
Zeng et al., Efficacy and safety of Seprafilm for preventing postoperative abdominal adhesion: Systematic review and meta-analysis. World J Surg 2007; 31:2125-2131.
U.S. Appl. No. 14/840,613, Medicant Eluting Adjuncts and Methods of Using Medicant Eluting Adjuncts, filed Aug. 31, 2015.
International Search Report for App. No. PCT/US2016/048181 dated Dec. 8, 2016 (3 pages).

* cited by examiner

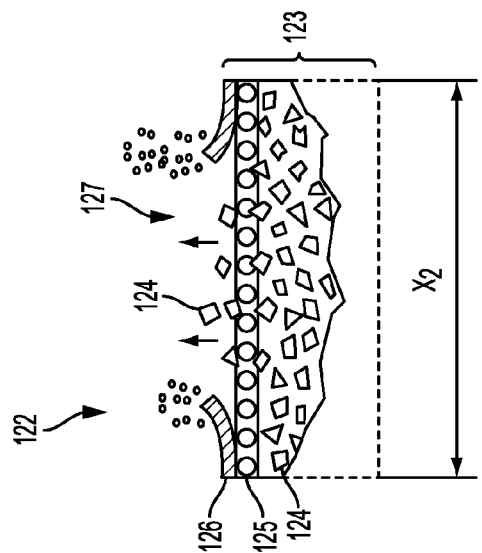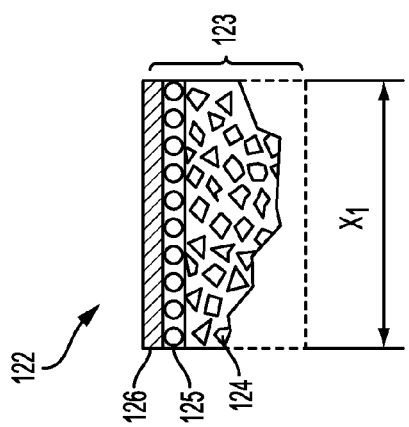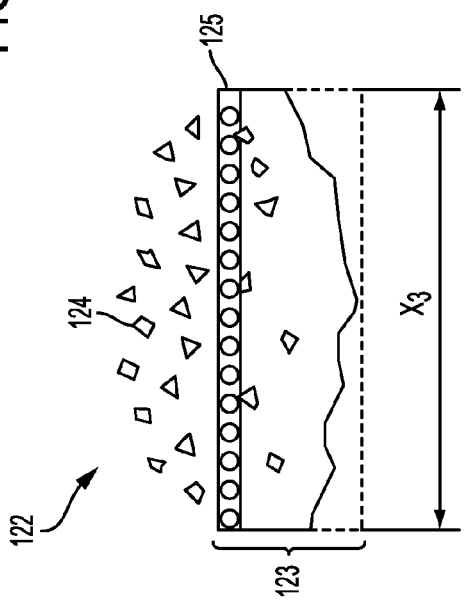

ADJUNCT MATERIAL TO PROVIDE CONTROLLED DRUG RELEASE

FIELD OF THE INVENTION

The present disclosure relates generally to adjunct material to release medicants therefrom in interdependent manner.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

In some instances, biologic materials have been used in conjunction with tissue stapling. However, the use of biologic materials presents a number of additional problems. For example, it can be difficult to maintain a location of the biologic material with respect to jaws of the stapler prior to and during staple ejection. It can also be difficult to keep the biologic material at a desired location at the surgical site after stapling is completed. Further, it can be difficult to manufacture the biologic material to a desired shape and thickness. Common plastic and molding manufacturing techniques are not generally conducive to the manufacture of thin biologic layers for use in conjunction with surgical staplers. The fragile nature of many biologic materials also makes them difficult to use with surgical staplers because they lack structural support.

Accordingly, there remains a need for improved devices and methods for stapling tissue, blood vessels, ducts, shunts, or other objects or body parts such that leaking and inflammation is minimized while substantially maintaining the natural characteristics of the treatment region. There further remains a need for improved implantable materials that include biologics.

SUMMARY

In general, adjunct material to provide release of at least first and second medicants therefrom such that release of a first medicant affects release of a second medicant is provided.

In one aspect, a staple cartridge assembly for use with a surgical stapler is provided that in some implementations includes a cartridge body having a plurality of staple cavities, each staple cavity having a surgical staple disposed therein, a bioabsorbable adjunct material releasably retained on the cartridge body and configured to be delivered to tissue by deployment of the staples in the cartridge body, a first medicant component associated with a component of the staple cartridge assembly in a manner in which the first medicant is released as a bolus dose substantially immediately upon delivery of the adjunct material to tissue, and a second medicant component associated with a component of the staple cartridge assembly in a manner such that release of the second medicant component to tissue is regulated by the release of the first medicant component.

The staple cartridge assembly can vary in a number of different ways. For example, the second medicant component can be configured to be released to tissue at a time after the release of the first medicant component. The second medicant component can be disposed within the adjunct material.

The second medicant component can be configured to be released to tissue over a period of time commencing at a time following release of the first medicant component. The second medicant component can be a first active agent disposed within a bioabsorbable polymer that is configured to be released from the first medicant component upon release of the first medicant component, and the first active agent can be configured to be released to tissue upon degradation of the bioabsorbable polymer.

The first and second medicant components can contain the same active agent. In some aspects, the first medicant component can be a second active agent that is different than the first active agent.

The release of the first medicant component can be configured to be triggered by mechanical disruption of a carrier for the first medicant component. In some aspects, the first medicant component can be disposed within a coating formed on the staples, and the mechanical disruption can be deformation of the staples. In some aspects, the first medicant component can be disposed within a staple line of the cartridge body, and the mechanical disruption can be puncture of a film retaining the first medicant within the staple line.

In other aspects, an end effector for a surgical instrument is provided that in some implementations includes a first jaw having a cartridge body removably attached thereto, the cartridge body having on a tissue-facing surface thereof a plurality of staple cavities configured to seat staples therein, a second jaw having an anvil with a plurality of staple forming cavities formed on a tissue-facing surface thereof, a biocompatible adjunct material releasably retained on at least one of the tissue-facing surfaces of the cartridge body first and the anvil and configured to be delivered to tissue by deployment of the staples in the cartridge body, a first medicant component associated with a component of the staple cartridge assembly in a manner in which the first medicant is released as a bolus dose substantially immediately upon delivery of the adjunct material to tissue, and a second medicant component associated with a component of the staple cartridge assembly in a manner such that release of the second medicant component to tissue is regulated by the release of the first medicant component. At least one of the first and second jaws is movable relative to the other.

The end effector can vary in a number of different ways. For example, the second medicant component can be configured to be released to tissue at a time after the release of the first medicant component. The second medicant component can be disposed within the adjunct material. The second medicant component can be configured to be released to tissue over a period of time commencing at a time following release of the first medicant component. The second medicant component can be a first active agent disposed within a bioabsorbable polymer that is configured to be released from the first medicant component upon release of the first medicant component, and the first active agent can be configured to be released to tissue upon degradation of the bioabsorbable polymer.

The first and second medicant components can contain the same active agent. The first medicant component can be a second active agent that is different than the first active agent.

The release of the first medicant component can be configured to be triggered by mechanical disruption of a carrier for the first medicant component. In some aspects, the first medicant component can be disposed within a coating formed on the staples, and the mechanical disruption can be deformation of the staples. In some aspects, the first medicant component can be disposed within a staple line of the cartridge body, and the mechanical disruption can be puncture of a film retaining the first medicant within the staple line.

BRIEF DESCRIPTION OF DRAWINGS

The present disclosure will be more fully understood from the following detailed description taken in conjunction with the accompanying drawings, in which:

FIG. 15 is a graphical representation of an adjunct material configured to release at least one medicant in response to at least one environmental condition;

FIG. 16 is a graphical representation of the adjunct material of FIG. 15, showing the at least one medicant partially released from the adjunct material in response to at least one environmental condition;

FIG. 17 is another graphical representation of the adjunct material of FIG. 15, showing the at least one medicant substantially entirely released from the adjunct material in response to at least one environmental condition;

DETAILED DESCRIPTION

Figure 1:
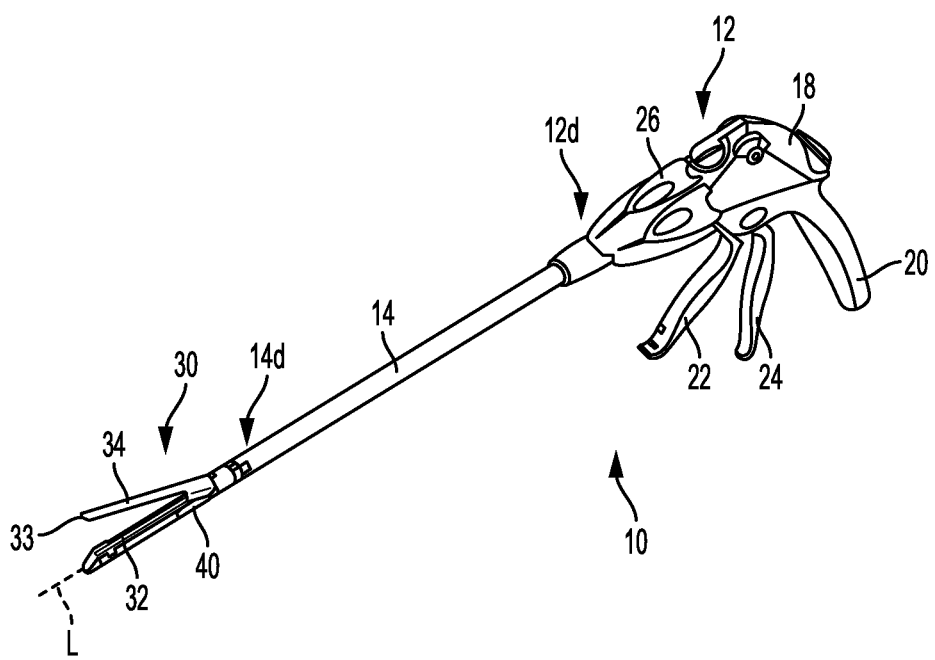
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s).

The adjunct(s) can also have medicant(s) thereon and/or therein. The medicant(s) can vary depending on the desired effect of the medicant(s) on the surrounding tissue. As a non-limiting example, medicant(s) can be provided to influence hemostasis, inflammation, macrophages, and/or fibroblasts. Medicant(s) can be mixed or combined in any combination or a medicant can be provided alone, again depending on the desired effect on the tissue. The medicant(s) can be eluted from the adjunct(s) in a variety of different ways. As non-limiting examples, coatings on the adjunct(s) can be varied to be absorbed at different times, thereby releasing the medicant(s) at different times; the adjunct(s) can be varied to allow diffusion of the medicant(s) across the adjunct(s) at varying rates; the adjunct(s) can vary in molecular weight and/or physical characteristics to cause release of the medicant(s) at different times; etc.

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used in a variety of different surgical procedures on a variety of tissues in a variety of different surgical procedures, for example in thoracic surgery or in gastric surgery.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. The lower jaw 32 has a staple channel 56 configured to support a staple cartridge 40, and the upper jaw 34 has an anvil surface 33 that faces the lower jaw 32 and that is configured to operate as an anvil to help deploy staples of the staple cartridge 40 (the staples are obscured in FIG. 1 and FIG. 2).

At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 or other cutting element can be associated with the firing system to cut tissue during the stapling procedure.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent a distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

Figure 2:
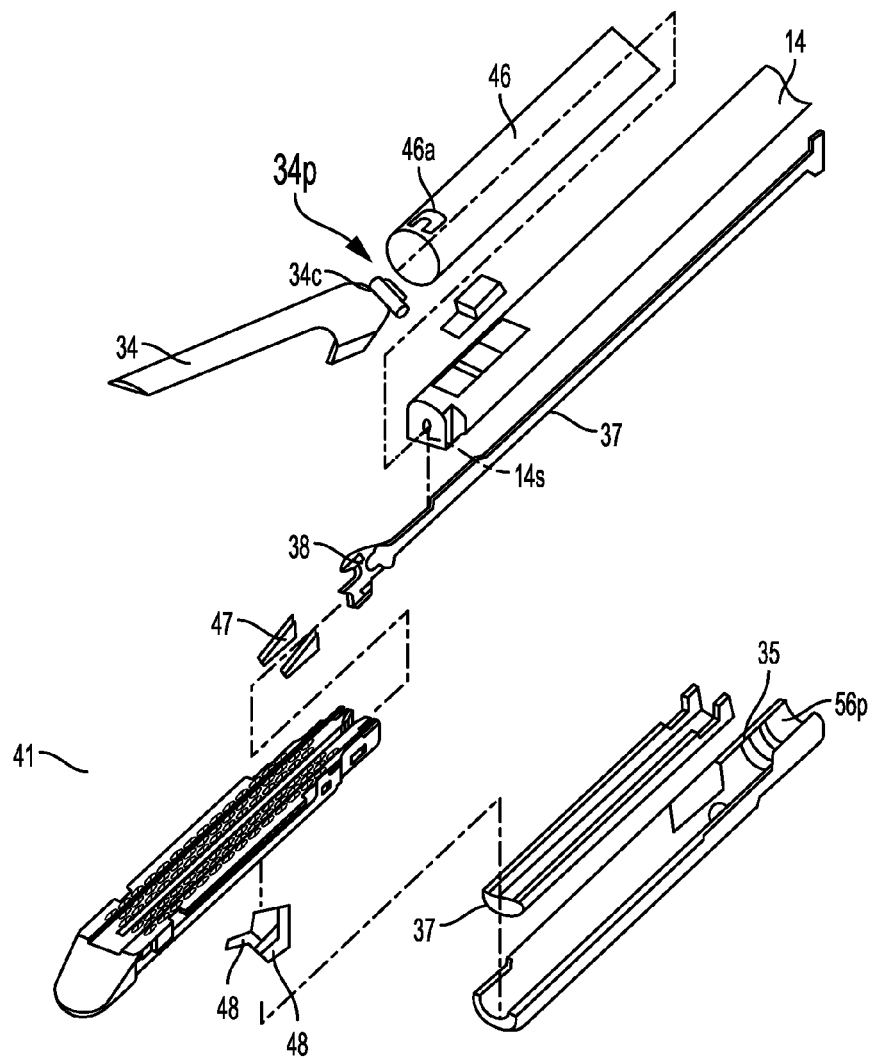
FIG. 2 is an exploded view of a distal portion of the surgical stapler of FIG. 1.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
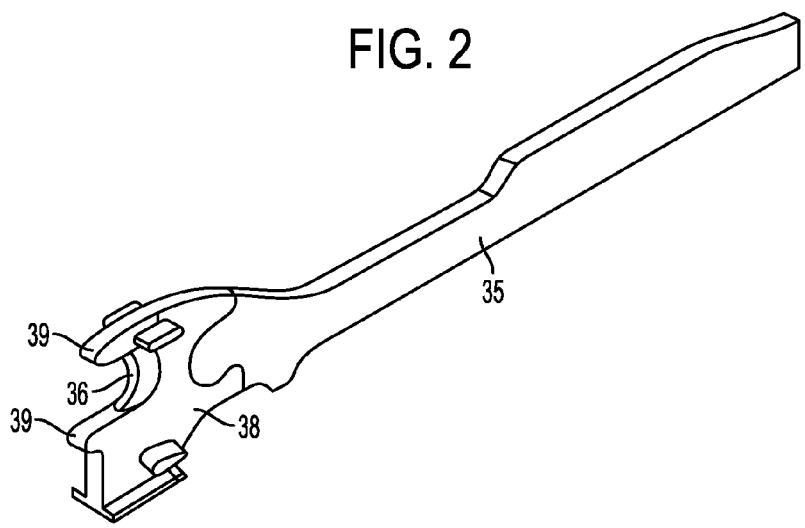
FIG. 3 is a perspective view of a firing bar of the surgical stapler of FIG. 1, the firing bar having an E-beam at a distal end thereof.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47 shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32,34 at the surgical site and the tissue with respect to the jaws 32, 34. After appropriate positioning has been achieved, the clamping trigger 22 can be pulled toward the stationary handle 20 to actuate the clamping system. The trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
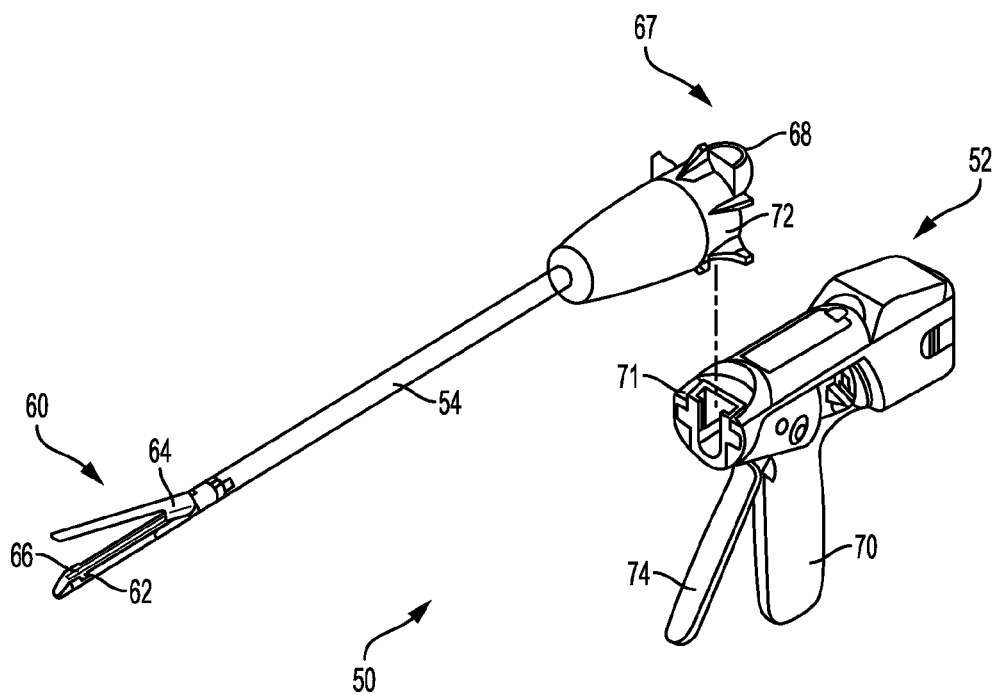
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
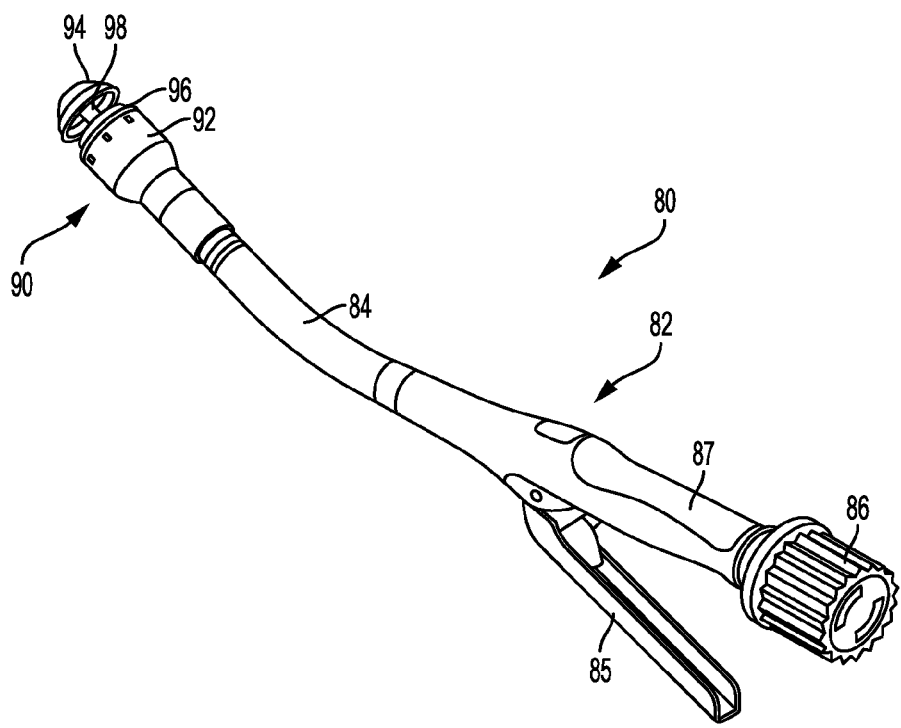
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIG. 1 and FIG. 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft can be disposed within the cartridge assembly 92 and extend distally outside of the cartridge assembly 92, terminating in a distal mating feature. The second portion of the shaft 84 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, i.e. move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, and 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. patent application Ser. No. 14/226,142, entitled "Surgical Instrument Comprising a Sensor System," and filed on Mar. 26, 2014, and U.S. patent application Ser. No. 14/300,954, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways, for example, it can be an extruded or a compression molded film.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

The adjunct can also be a hybrid construct, such as a laminate composite or melt-locked interconnected fiber. Examples of various hybrid construct adjuncts are further described in U.S. Pat. Pub. No. 2013/0146643 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

Materials

The adjuncts in accordance with the described techniques can be formed from various materials. The materials can be used in various embodiments for different purposes. The materials can be selected in accordance with a desired therapy to be delivered to tissue so as to facilitate tissue in-growth. The materials described below can be used to form an adjunct in any desired combination.

The materials can include bioabsorbable and biocompatible polymers, including homopolymers and copolymers. Non-limiting examples of homopolymers and copolymers include p-dioxanone (PDO or PDS), polyglycolic acid (PGA), poly(lactic-co-glycolic acid) (PLGA), polycaprolactone (PCL), trimethylene carbonate (TMC), and polylactic acid (PLA), poly(glycolic acid-co-lactic acid) (PLA/PGA) (e.g., PLA/PGA materials used in Vicryl, Vicryl Rapide, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides, and tyrosine-based polyesteramides. The copolymers can also include poly(lactic acid-co-polycaprolactone) (PLA/PCL), poly(L-lactic acid-co-polycaprolactone) (PLLA/PCL), poly(glycolic acid-co-trimethylene carbonate) (PGA/TMC) (e.g., Maxon), Poly(glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), and LPLA/DLPLA (e.g., Optima).

An adjunct can also include active agents, such as active cell culture (e.g., diced autologous tissue, agents used for stem cell therapy (e.g., Biosutures and Cellerix S.L.), hemostatic agents, and tissue healing agents. Non-limiting examples of hemostatic agents can include cellulose such as oxidized Regenerated Cellulose (ORC) (e.g., Surgicel and Interceed), fibrin/thrombin (e.g., Thrombin-JMI, TachoSil, Tiseel, Floseal, Evicel, TachoComb, Vivostat, and Everest), autologous platelet plasma, gelatin (e.g., Gelfilm and Gelfoam), hyaluronic acid such as microfibers (e.g., yarns and textiles) or other structures based on hyaluronic acid, or hyaluronic acid-based hydrogels. The hemostatic agents can also include polymeric sealants such as, for example, bovine serum albumin and glutarldehyde, human serum albumin and polyethylene cross-linker, and ethylene glycol and trimethylene carbonate. The polymeric sealants can include FocalSeal surgical sealant developed by Focal Inc.

The adjuncts described herein can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response.

Non-limiting examples of antimicrobial agents include Ionic Silver, Aminoglycosides, Streptomycin, Polypeptides, Bacitracin, Triclosan, Tetracyclines, Doxycycline, Minocycline, Demeclocycline, Tetracycline, Oxytetracycline, Chloramphenicol, Nitrofurans, Furazolidone, Nitrofurantoin, Beta-lactams, Penicillins, Amoxicillin, Amoxicillin+, Clavulanic Acid, Azlocillin, Flucloxacillin, Ticarcillin, Piperacillin+tazobactam, Tazocin, Biopiper TZ, Zosyn, Carbapenems, Imipenem, Meropenem, Ertapenem, Doripenem, Biapenem, Panipenem/betamipron, Quinolones, Ciprofloxacin, Enoxacin, Gatifloxacin, Gemifloxacin, Levofloxacin, Lomefloxacin, Moxifloxacin, Nalidixic Acid, Norfloxacin, Sulfonamides, Mafenide, Sulfacetamide, Sulfadiazine, Silver Sulfadiazine, Sulfadimethoxine, Sulfamethizole, Sulfamethoxazole, Sulfasalazine, Sulfisoxazole, Bactrim, Prontosil, Ansamycins, Geldanamycin, Herbimycin, Fidaxomicin, Glycopeptides, Teicoplanin, Vancomycin, Telavancin, Dalbavancin, Oritavancin, Lincosamides, Clindamycin, Lincomycin, Lipopeptide, Daptomycin, Macrolides, Azithromycin, Clarithromycin, Erythromycin, Roxithromycin, Telithromycin, Spiramycin, Oxazolidinones, Linezolid, Aminoglycosides, Amikacin, Gentamicin, Kanamycin, Neomycin, Netilmicin, Tobramycin, Paromycin, Paromomycin, Cephalosporins, Ceftobiprole, Ceftolozane, Cefclidine, Flomoxef, Monobactams, Aztreonam, Colistin, and Polymyxin B.

Non-limiting examples of antifungal agents include Triclosan, Polyenes, Amphotericin B, Candicidin, Filipin, Hamycin, Natamycin, Nystatin, Rimocidin, Azoles, Imidazole, Triazole, Thiazole, Allylamines, Amorolfin, Butenafine, Naftifine, Terbinafine, Echinocandins, Anidulafungin, Caspofungin, Micafungin, Ciclopirox, and Benzoic Acid.

Non-limiting examples of antiviral agents include uncoating inhibitors such as, for example, Amantadine, Rimantadine, Pleconaril; reverse transcriptase inhibitors such as, for example, Acyclovir, Lamivudine, Antisenses, Fomivirsen, Morpholinos, Ribozymes, Rifampicin; and virucidals such as, for example, Cyanovirin-N, Griffithsin, Scytovirin, α-Lauroyl-L-arginine ethyl ester (LAE), and Ionic Silver.

Non-limiting examples of anti-inflammatory agents include non-steroidal anti-inflammatory agents (e.g., Salicylates, Aspirin, Diflunisal, Propionic Acid Derivatives, Ibuprofen, Naproxen, Fenoprofen, and Loxoprofen), acetic acid derivatives (e.g., Tolmetin, Sulindac, and Diclofenac), enolic acid derivatives (e.g., Piroxicam, Meloxicam, Droxicam, and Lornoxicam), anthranilic acid derivatives (e.g., Mefenamic Acid, Meclofenamic Acid, and Flufenamic Acid), selective COX-2 inhibitors (e.g., Celecoxib (Celebrex), Parecoxib, Rofecoxib (Vioxx), Sulfonanilides, Nimesulide, and Clonixin), immune selective anti-inflammatory derivatives, corticosteroids (e.g., Dexamethasone), and iNOS inhibitors.

Non-limiting examples of growth factors include those that are cell signaling molecules that stimulate cell growth, healing, remodeling, proliferation, and differentiation. Exemplary growth factors can be short-ranged (paracrine), long ranged (endocrine), or self-stimulating (autocrine). Further examples of the growth factors include growth hormones (e.g., a recombinant growth factor, Nutropin, Humatrope, Genotropin, Norditropin, Saizen, Omnitrope, and a biosynthetic growth factor), Epidermal Growth Factor (EGF) (e.g., inhibitors, Gefitinib, Erlotinib, Afatinib, and Cetuximab), heparin-binding EGF like growth factors (e.g., Epiregulin, Betacellulin, Amphiregulin, and Epigen), Transforming Growth Factor alpha (TGF-a), Neuroregulin 1-4, Fibroblast Growth Factors (FGFs) (e.g., FGF1-2, FGF2, FGF11-14, FGF18, FGF15/19, FGF21, FGF23, FGF7 or Keratinocyte Growth Factor (KGF), FGF10 or KGF2, and Phenytoin), Insuline-like Growth Factors (IGFs) (e.g., IGF-1, IGF-2, and Platelet Derived Growth Factor (PDGF)), Vascular Endothelial Growth Factors (VEGFs) (e.g., inhibitors, Bevacizumab, Ranibizumab, VEGF-A, VEGF-B, VEGF-C, VEGF-D and Becaplermin).

Additional non-limiting examples of the growth factors include cytokines, such as Granulocyte Macrophage Colony Stimulating Factors (GM-CSFs) (e.g., inhibitors that inhibit inflammatory responses, and GM-CSF that has been manufactured using recombinant DNA technology and via recombinant yeast-derived sources), Granulocyte Colony Stimulating Factors (G-CSFs) (e.g., Filgrastim, Lenograstim, and Neupogen), Tissue Growth Factor Beta (TGF-B), Leptin, and interleukins (ILs) (e.g., IL-1a, IL-1b, Canakinumab, IL-2, Aldesleukin, Interking, Denileukin Diftitox, IL-3, IL-6, IL-8, IL-10, IL-11, and Oprelvekin). The non-limiting examples of the growth factors further include erythropoietin (e.g., Darbepoetin, Epocept, Dynepo, Epomax, Neo-Recormon, Silapo, and Retacrit).

Non-limiting examples of analgesics include Narcotics, Opioids, Morphine, Codeine, Oxycodone, Hydrocodone, Buprenorphine, Tramadol, Non-Narcotics, Paracetamol, acetaminophen, NSAIDS, and Flupirtine.

Non-limiting examples of anesthetics include local anesthetics (e.g., Lidocaine, Benzocaine, and Ropivacaine) and general anesthetic.

Non-limiting examples of tissue matrix degradation inhibitors that inhibit the action of metalloproteinases (MMPs) and other proteases include MMP inhibitors (e.g., exogenous MMP inhibitors, hydroxamate-based MMP inhibitors, Batimastat (BB-94), Ilomastat (GM6001), Marimastat (BB2516), Thiols, Periostat (Doxycycline), Squaric Acid, BB-1101, Hydroxyureas, Hydrazines, Endogenous, Carbamoylphosphates, Beta Lactams, and tissue Inhibitors of MMPs (TIMPs)).

Non-limiting examples of anti-cancer agents include monoclonial antibodies, bevacizumab (Avastin), cellular/chemoattractants, alkylating agents (e.g., Bifunctional, Cyclophosphamide, Mechlorethamine, Chlorambucil, Melphalan, Monofunctional, Nitrosoureas and Temozolomide), anthracyclines (e.g., Daunorubicin, Doxorubicin, Epirubicin, Idarubicin, Mitoxantrone, and Valrubicin), cytoskeletal disrupters (e.g., Paclitaxel and Docetaxel), epothilone agents that limit cell division by inhibiting microtubule function, inhibitor agents that block various enzymes needed for cell division or certain cell functions, histone deacetylase inhibitors (e.g., Vorinostat and Romidepsin), topoisomerase I inhibitors (e.g., Irinotecan and Topotecan), topoisomerase II inhibitors (e.g., Etoposide, Teniposide, and Tafluposide), kinase inhibitors (e.g., Bortezomib, Erlotinib, Gefitinib, Imatinib, Vemurafenib, and Vismodegib), nucleotide analogs (e.g., Azacitidine, Azathioprine, Capecitabine, Cytarabine, Doxifluridine, Fluorouracil, 5-FU, Adrucil, Carac, Efudix, Efudex, Fluoroplex, Gemcitabine, Hydroxyurea, Mercaptopurine, and Tioguanine), peptide antibiotic agents that cleave DNA and disrupt DNA unwinding/winding (e.g., Bleomycin and Actinomycin), platinum-based anti-neoplastic agents that cross link DNA which inhibits DNA repair and/or synthesis (e.g., Carboplatin, Cisplatin, Oxaliplatin, and Eloxatin), retinoids (e.g., Tretinoin, Alitretinoin, and Bexarotene), vinca alkaloids gents that inhibit mitosis and microtubule formation (e.g., Vinblastine, Vincristine, Vindesine, Vinorelbine), anti-ileus agents, pro-motility agents, immunosuppressants (e.g., Tacrolimus), blood aspect modifier agents (e.g., Vasodilator, Viagra, and Nifedipine), 3-hydroxy-3-methyl-glutaryl-CoA (HMG CoA) reductase inhibitors (e.g., Atorvastatin), and anti-angiogenesis agents.

Exemplary medicants also include agents that passively contribute to wound healing such as, for example, nutrients, oxygen expelling agents, amino acids, collageno synthetic agents, Glutamine, Insulin, Butyrate, and Dextran. Exemplary medicants also include anti-adhesion agents, non-limiting examples of which include Hyaluronic acid/Carboxymethyl cellulose (seprafilm), Oxidized Regenerated Cellulose (Interceed), and Icodextrin 4% (Extraneal, Adept).

Drug Release

An adjunct in accordance with the described techniques can be associated with at least one medicant in a number of different ways, so as to provide a desired effect, such as on tissue in-growth, in a desired manner. The at least one medicant can be configured to be released from the adjunct in multiple spatial and temporal patterns to trigger a desired healing process at a treatment site. The medicant can be disposed within, bonded to, incorporated within, dispersed within, or otherwise associated with the adjunct. For example, the adjunct can have one or more regions releasably retaining therein one or more different medicants. The regions can be distinct reservoirs of various sizes and shapes and retaining medicants therein in various ways, or other distinct or continuous regions within the adjuncts. In some aspects, a specific configuration of the adjunct allows it to releasably retain therein a medicant or more than one different medicant.

Regardless of the way in which the medicant is disposed within the adjunct, an effective amount of the at least one medicant can be encapsulated within a vessel, such as a pellet which can be in the form of microcapsules, microbeads, or any other vessel. The vessels can be formed from a bioabsorbable polymer.

Targeted delivery and release of at least one medicant from an adjunct can be accomplished in a number of ways which depend on various factors. In general, the at least one medicant can be released from the adjunct material as a bolus dose such that the medicant is released substantially immediately upon delivery of the adjunct material to tissue. Alternatively, the at least one medicant can be released from the adjunct over a certain duration of time, which can be minutes, hours, days, or more. A rate of the timed release and an amount of the medicant being released can depend on various factors, such as a degradation rate of a region from which the medicant is being released, a degradation rate of one or more coatings or other structures used to retains the medicant within the adjuncts, environmental conditions at a treatment site, and various other factors. In some aspects, when the adjunct has more than one medicant disposed therein, a bolus dose release of a first medicant can regulate a release of a second medicant that commences release after the first medicant is released. The adjunct can include multiple medicants, each of which can affect the release of one or more other medicants in any suitable way.

Release of at least one medicant as a bolus dose or as a timed release can occur or begin either substantially immediately upon delivery of the adjunct material to tissue, or it can be delayed until a predetermined time. The delay can depend on a structure and properties of the adjunct or one or more of its regions.

An adjunct material can be configured to have a structure that facilitates distribution of effective amounts of one or more medicants carried within the adjunct to provide a desired effect. For example, the targeted delivery of the medicants can be accomplished by incorporating the medicants into regions (e.g., reservoirs such as pores or other structures) within the adjunct formed in a pattern that allows a certain spatial distribution of the medicants upon their delivery. The medicants disposed within the reservoir can be incorporated into distinct vessels. A reservoir can include more than one type of different medicants. The one or more medicants can be eluted from the adjunct in a homogeneous manner or in heterogeneous spatial and/or temporal manner to deliver a desired therapy. The structure of the adjunct and the way in which the medicants are released therefrom can be used to influence or control tissue re-growth. Moreover, the tissue regrowth can be encouraged in certain locations at the treatment site and discouraged at other locations at the treatment site.

Figures 6, 7:
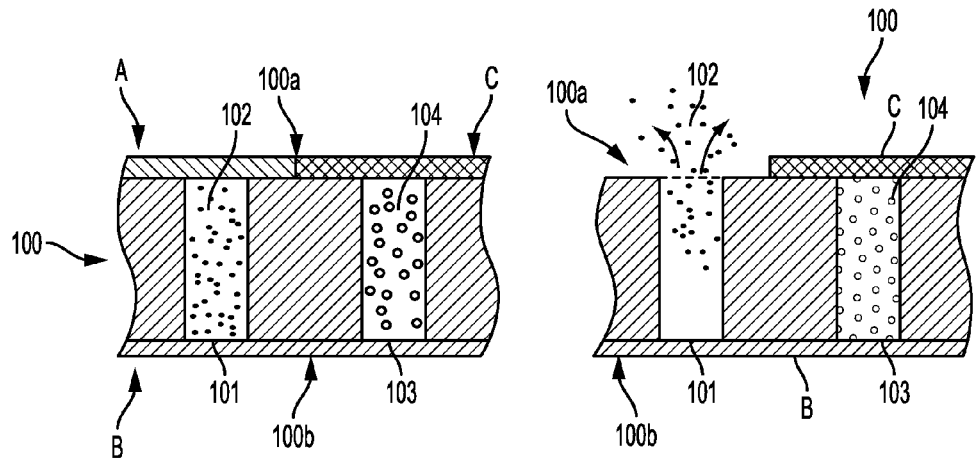
FIG. 6 is a graphical representation of an embodiment of an adjunct material with different types of medicants encapsulated using different release mechanisms before medicant release.
FIG. 7 is a graphical representation of the adjunct material of FIG. 6, showing release of a first medicant.
Figure 8:
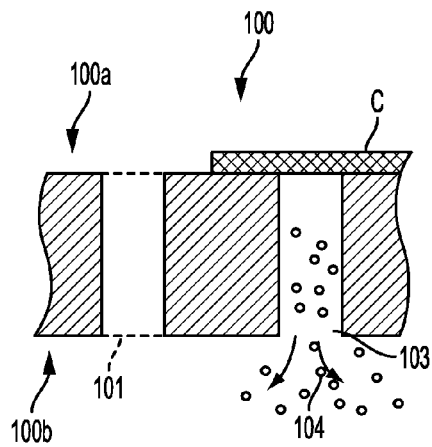
FIG. 8 is a graphical representation of the adjunct material of FIG. 6, showing release of a second medicant.

FIG. 6 through FIG. 8 illustrate a biocompatible adjunct 100 having multiple pores carrying different medicants that are encapsulated within the pores disposed at different locations and using different absorbable coatings. The coatings can absorb, dissolve or otherwise disintegrate at different times after delivery of the adjunct 100 to a treatment site and staple deployment so as to allow the medicants to also release at different times and in different directions. Thus, the medicants can be released from the adjunct 100 in a non-homogeneous manner. For example, one of the medicants can be released immediately after delivery and/or staple deployment whereas one or more of other medicants can be released at a later time, such as over a predetermined release profile. The release of these subsequently released medicants can be controlled by or depend upon the release of the first medicant. The opposite sides of the adjunct 100 can be covered by coatings (or be formed of materials) having different absorption rates such that certain medicant(s) are released on one side of the adjunct while other medicant(s) are released on another side of the adjunct. This provides a more controlled and targeted way of delivering therapies to tissue.

In this example, the adjunct 100 is in the form of a layer having multiple porous regions, two of which are shown by way of example as pores 101, 103. As shown in FIG. 6, the porous regions 101, 103 carry respective first and second medicants 102, 104 which can be different medicants. It should be appreciated that the adjunct 100 has multiple porous regions which can carry the medicants 102, 104 in an alternating manner or in any other patterns.

As shown in FIG. 6, a first side 100a of the adjunct 100 has coatings A, C such that the coating A seals the porous region 101 with the first medicant 102 and the coating C seals the porous region 103 with the second medicant 104. A second, opposite side 100b of the adjunct 100 is covered by a coating B. In the illustrated example, the coatings A, B, C that create a barrier that affects release of a medicant can be selected such that the coating A absorbs first after the staple deployment, the coating B absorbs after the coating A has been at least partially absorbed, and the coating C is not absorbable.

As shown in FIG. 7, after the delivery and/or staple deployment, the coating A is first absorbed so as to allow the first medicant 102 to be released from the porous region 101 at the first side 100a of the adjunct 100. For example, if the first side 100a is a tissue-contacting surface, the first medicant 102 can be a medicant that promotes healing at the treatment site. Subsequently, after a certain time period, the coating B can be absorbed so as to allow the second medicant 104 to be released from the porous region 103 at the second side 100b of the adjunct 100, as shown in FIG. 8. For example, if the second side 100b is a non-tissue-contacting surface, the second medicant 104 can be a medicant that prevents adhesion. As also shown in FIG. 8, the coating C seals the porous region 103 at the first side 100a and thus prevents the second medicant 104 from being released at the first side 100a of the adjunct 100. Although in this example the coating C is not absorbable, it can alternatively be absorbable after the coating B has been absorbed and the second medicant 104 can been released at the second side 100b. It should be appreciated that, to allow a porous region to be exposed and a medicant to release, a coating can be absorbed in its entirety or at least partially. A rate of absorption of a coating can control a rate of release of a medicant.

A person skilled in the art will appreciate that more than two different medicants can be releasably incorporated into different porous regions or other structures within an adjunct. The medicants can be retained within the adjunct using various coatings that can be selected so as to control rate and direction of release of the medicants.

Figure 9:
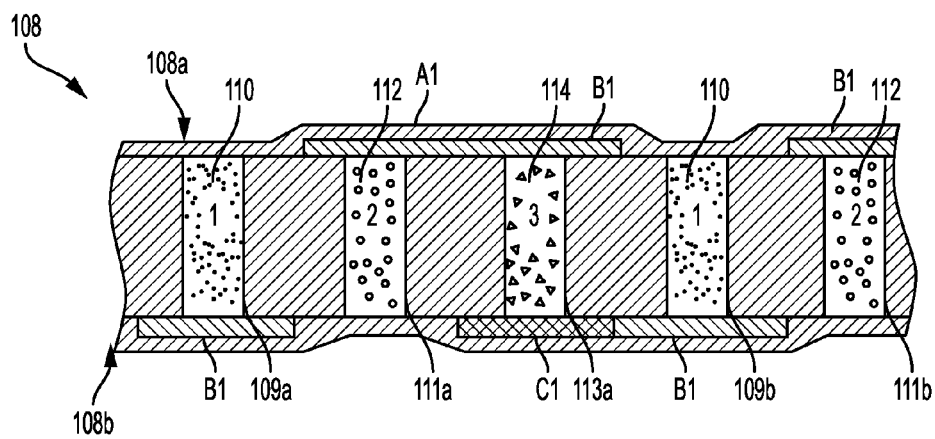
FIG. 9 is another graphical representation of an embodiment of an adjunct material with different types of medicants encapsulated using different release mechanisms before medicant release.
Figure 10:
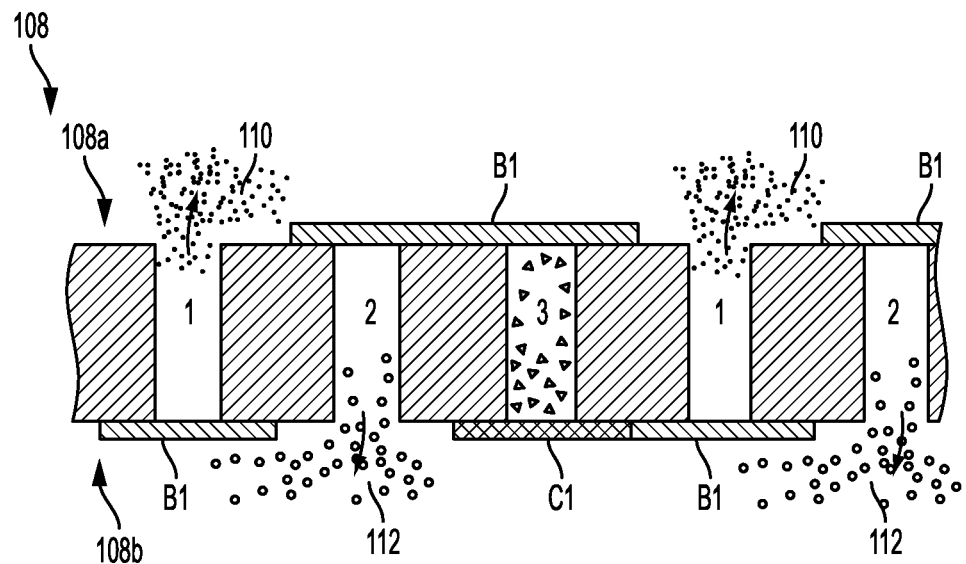
FIG. 10 is a graphical representation of the adjunct material of FIG. 9, showing release of the medicants as a result of absorption of a first coating.
Figure 11:
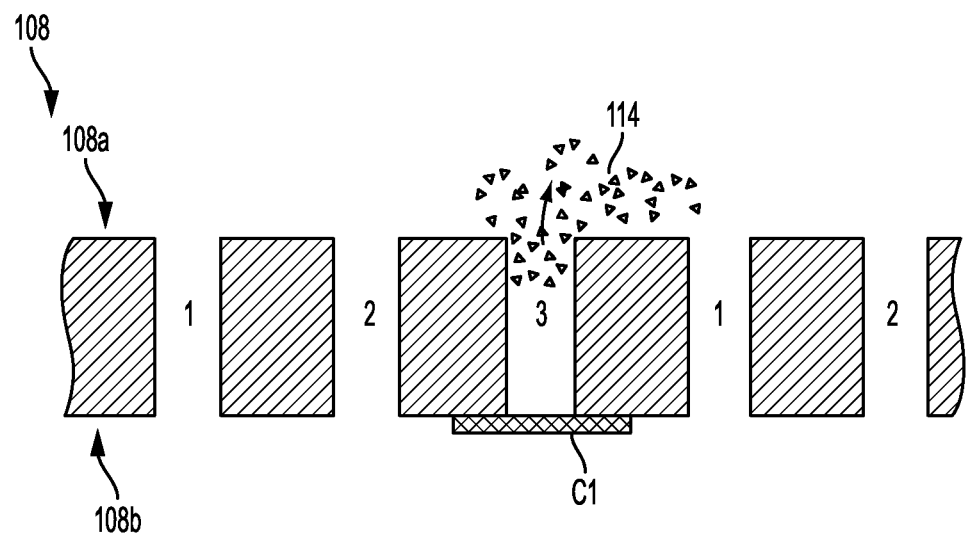
FIG. 11 is a graphical representation of the adjunct material of FIG. 9, showing release of the medicants as a result of absorption of a second coating.

An adjunct can include regions (e.g., pores or other reservoirs) releasably retaining a plurality of vessels, such as micro beads or other vessels, that have one or more medicants encapsulated therein. FIG. 9 through FIG. 11 illustrate an adjunct 108 including at least one medicant encapsulated in a plurality of vessels that are releasably retained by respective regions that regulate the dispersion of the vessels from the adjunct. The vessels can be micro capsules, micro beads, or any other types of vessels of a suitable size and shape. Each vessel can have an absorbable outer layer that can degrade and thus release a medicant retained within that vessel once the vessels are released from an adjunct. The adjunct can be used to deliver medicants in a non-homogeneous manner with respect to at least time of release and location of release.

As shown in FIG. 9, the adjunct 108 has multiple reservoirs or regions, five of which are shown as regions 109a, 111a, 113a, 109b, 111b that carry respective vessels 110, 112, 114, 110, 112. Thus, as shown schematically in FIG. 9, the regions 109a, 109b carry the same first type of vessels 110, the regions 111a, 111b carry the same second type of vessels 112, and the region 113a carries a third type of vessels 114.

As shown in FIG. 9, on a first side 108a of the adjunct 108, a layer of coating B1 seals the regions 111a, 113a and the region 111b. A layer of a coating A1 is disposed over the entire first side 108a and covers the layers of the coating B1. On a second, opposite side 108b of the adjunct 108, a layer of the coating B1 seals the region 109a and another layer of the coating B1 seals the region 109b. A layer of a coating C1 seals the region 113a on the second side 108b. Similar to the first side 108a, the entire second side 108b is covered by the coating A1.

In this example, the coatings A1, B1, C1 have different degradation or absorption rates such that the coating A1 begins to absorb first, upon a delivery of the adjunct to tissue, the coating B1 absorbs after the coating A1 is at least partially absorbed, and the coating C1 is not absorbable. The coating A1 can be selected such that it absorbs substantially immediately after the delivery of the adjunct to tissue or at some later time. The coating A1 can be absorbed before the coating B1 because the coating A1 is disposed on the surface of the adjunct and is therefore more accessible to water and/or other agents at a treatment side. Other properties of the coating A1 can contribute to its absorption rate additionally or alternatively.

Because of the different absorption characteristics of the coating used, the coating A1 absorbs so as to release the first medicant 110 from the regions 109a, 109b at the first side 108a and to release the second medicant 112 from the regions 111a, 111b at the second side 108b, as shown in FIG. 10. As also shown in FIG. 10, the layers of the coating B1 remain associated with the adjunct 108. As shown in FIG. 11, after the first medicant 110 is released at the first side 108a and the second medicant 112 is released at the second side 108b, the coating B1 absorbs so as to release the third medicant 114 from the region 113a at the first side 108a. In this way, different medicants can be delivered at appropriate times to desired locations in tissue being treated. It should be appreciated that an adjunct can have any suitable pattern of regions releasably retaining various medicants to create a desired healing process/profile.

In some aspects, alternatively or in addition to using various coatings, an adjunct can be in a form of a fiber lattice having regions with different absorption characteristics. For example, each of the regions can be in the form of fiber lattices having different absorption rates. A medicant associated with a fiber lattice can be released as the fiber lattice disintegrates. Because of the heterogeneous degradation of absorbable polymers forming the adjunct, the adjunct can be configured such that one or more medicants associated therewith can release in various spatial and temporal patterns. The medicant can be incorporated into pellets having a dissolvable coating (e.g., like a gobstopper) such that, as the coating is disintegrated, the medicant can be distributed as a bolus dose or as a time release dosage.

Figure 12:
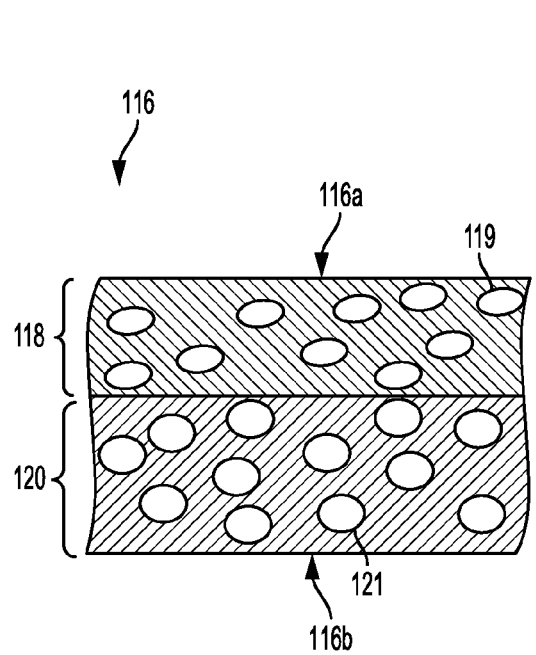
FIG. 12 is a graphical representation of an adjunct material including top and bottom layers of an absorbable polymer having different degradation rates.
Figure 13:
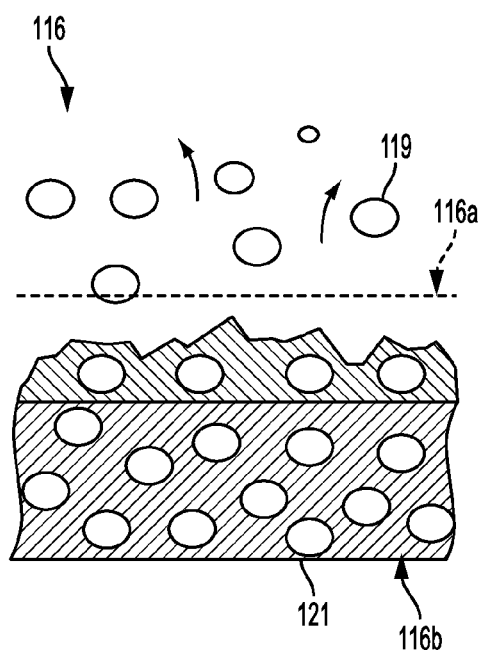
FIG. 13 is a graphical representation of the adjunct material of FIG. 12, showing a top layer partially degraded.
Figure 14:
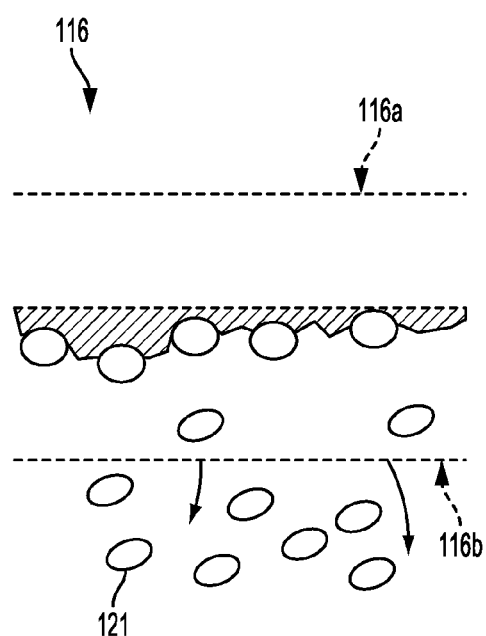
FIG. 14 is a graphical representation of the adjunct material of FIG. 12, showing a bottom layer partially degraded after the top layer has been degraded.

FIG. 12 through FIG. 14 illustrate an adjunct 116 having first (top) and second (bottom) layers 118, 120 formed from absorbable polymers having different degradation rates. For example, the first layer 118 can be a low molecular weight absorbable polymer that absorbs during a first time period after the adjunct 116 is delivered to tissue and the second layer 120 can be a high molecular weight absorbable polymer that absorbs during a second time period after the first time period is completed. The first and second layers 118, 120 can be formed from different polymers or from the same type of polymer that is treated so as to form layers or other structures having different degradation properties.

In the example of FIG. 12 through FIG. 14, the first layer 118 has a first medicant 119 present therein, and the second layer 120 has second medicant 121 present therein. It should be appreciated, however, that each of the first and second layers 118, 120 can include more than one type of different medicant. The medicants can be retained in association with the first and second layers 118, 120 in a number of suitable ways. The first medicant 119 can be released first due to absorption of the first layer 118, as shown in FIG. 13 where the first layer 118 is shown partially disintegrated such that the pellets containing the first medicant 119 are being released. As shown, the first layer 118 begins to absorb from its surface that is more accessible to water and other agents than portions of the first layer 118 removed farther from the surface. After the first layer 118 has been entirely or partially absorbed, the second layer 120 can commence to disintegrate from its surface so as to release pellets harboring the second medicant 121, as shown in FIG. 14 where the second layer 120 is shown partially disintegrated and the pellets containing the second medicant 121 are being released from the adjunct 116.

In some aspects, an adjunct releasably retaining one or more medicants can be configured such that one or more regions of the adjunct disintegrate due to effects of temperature, pH, light, or other environmental factors so as to release the medicant(s). Alternatively, the adjunct can break under the strain exerted upon one or more of its portions. FIG. 15 through FIG. 17 illustrate an adjunct 122 having a body 123 retaining a medicant 124, a porous layer 125 disposed over the body 123, and an absorbable outer film layer 126 disposed over the porous layer 125. The medicant 124 can be in the form of pellets (e.g., solid micro-capsules or micro-beads or other vessels) releasably carrying one or more medicants.

In the example illustrated, in its original configuration, the adjunct 122 has a first width X1, as shown in FIG. 15. In such configuration, the outer film layer 126 restrains the porous layer 125 and pores in the porous layer 125 have a size that does not allow the medicant 124 to escape the adjunct 122. However, when the adjunct 122 is delivered to tissue and the outer film layer 126 thus becomes exposed to pH, temperature, various agents, and/or other environmental conditions at the treatment site, the absorbable outer film layer 126 can begin to disintegrate, as shown by a tear or opening 127 in the film layer 126 in FIG. 16. Additionally or alternatively, the outer film layer 126 can break upon strain due to deployment of staples or other mechanical strain on the adjunct 122.

Regardless of the specific factors that result in disintegration or breaking of the outer film layer 126, the adjunct 122 can swell or otherwise alter its conformation such that its width increases from the original width X1 to a larger width X2. As also shown in FIG. 15, the size of the pores of porous layer 125 increases, allowing the pores' content, the pellets carrying the medicant 124, to pass through the enlarged pores and to be thus released from the adjunct 122.

A period of time during which the adjunct body 123 expands and the pellets with the medicant 124 are released can vary based on an absorption rate of the outer film 126, properties of the adjunct body 123, characteristics of the environment to which the adjunct 122 is delivered, and other factors. After a certain time period, the outer film layer 126 can disintegrate and the adjunct 122 can expand further to have a width X3 such that the entirety or substantially the entirety of the medicant 124 becomes released from the body 123 to deliver appropriate therapy or achieve the desired effect, as shown in FIG. 17. The adjunct 122 can be formed from at least one absorbable polymer (e.g., gelatin, cellulose, etc.) that regulates dispersion of the vessels. Thus, the adjunct 122 can act as a space filler that creates a temporary seal at a treatment site and is then dissolved to be subsequently replaced with tissue.

Figure 18:
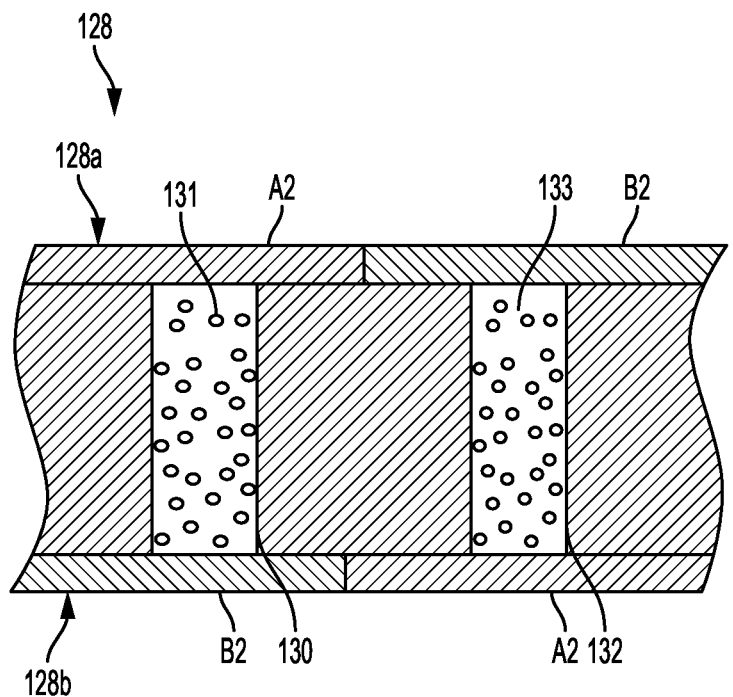
FIG. 18 is a graphical representation of an adjunct material configured to release at least one medicant by changing its conformation.
Figure 19:
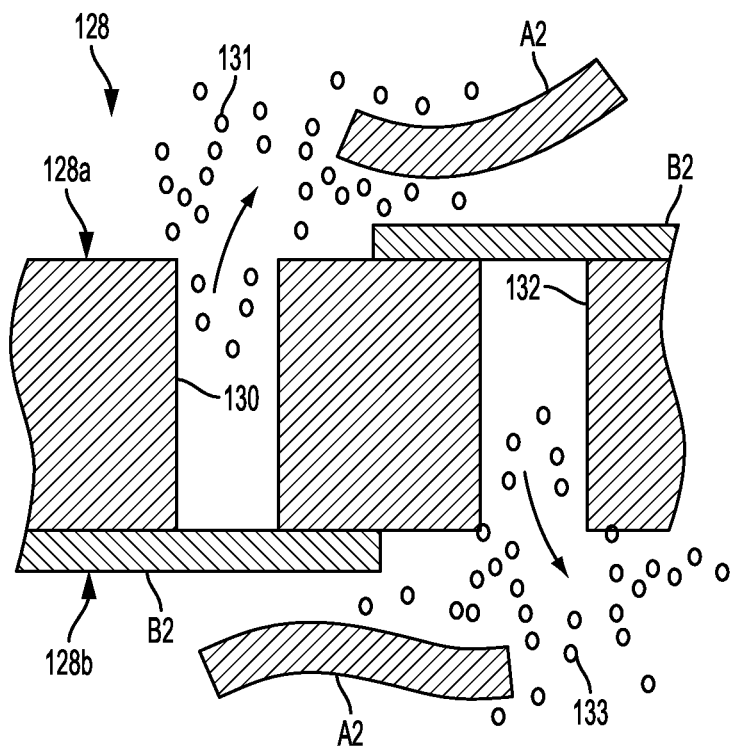
FIG. 19 is a graphical representation of the adjunct material of FIG. 18, showing the adjunct material with its conformation changes and the at least one medicant partially released.

FIG. 18 and FIG. 19 illustrate another example of an adjunct 128 releasably retaining different medicants and configured to release the medicants in a non-homogeneous manner. The adjunct 128 can be configured to release the medicants due the effects of temperature, pH, various agents, and/or other environmental factors upon the adjunct 128. The adjunct 128 can change a conformation of one or more of its portions in response to the environmental factors. As shown in FIG. 18, the adjunct 128 can have multiple regions or reservoirs two of which, first and second reservoirs 130, 132 carrying first and second medicants 131, 133, respectively, are shown. The reservoirs 130, 132 can be in the form of tubes, cavities, holes, or any other structures. The first reservoir 130 is sealed by a first coating A2 at a first side 128a of the adjunct 128 and by a second coating B2 at a second side 128b of the adjunct 128. The second reservoir 131 is sealed by the second coating B2 at the first side 128a and by the first coating A2 at the second side 128. In this example, the first and second coatings A2, B2 are selected such that the first coating A2 and its properties and/or configuration can be altered by the effects of temperature, pH, active agents, and/or other factors and thus open a reservoir that it seals. For example, the first coating A2 can swell, soften, or otherwise become altered.

Accordingly, as shown in FIG. 19, upon the delivery of the adjunct 128 to a treatment site, the first coating A2 can change its configuration such that it no longer seals the reservoir 130 at the first side 128a of the adjunct 128 and it no longer seals the reservoir 132 at the second side 128b of the adjunct 128. As a result, the first and second medicants 131, 133 are released at the first and second sides 128a, 128b of the adjunct, respectively, as also shown in FIG. 19. The second coating B2 remains in place at least until the entirety of the medicants are released into desired tissue locations, such preventing the release of the medicants.

In some aspects, the adjunct can be in the form of fibers or other structural components associated with one or more viscous fluid components (e.g., vessels) retaining the medicant. The viscous component can be in a dry form (e.g., in a freeze-dried powder form) and it can re-hydrate upon deployment of the adjunct. As the viscous component rehydrates, it can open and thus release a medicant. Additionally or alternatively, the vessel retaining the medicant can be disrupted by strain such as, for example, mechanical breaking imposed thereon by the staples or other means.

Figure 20:
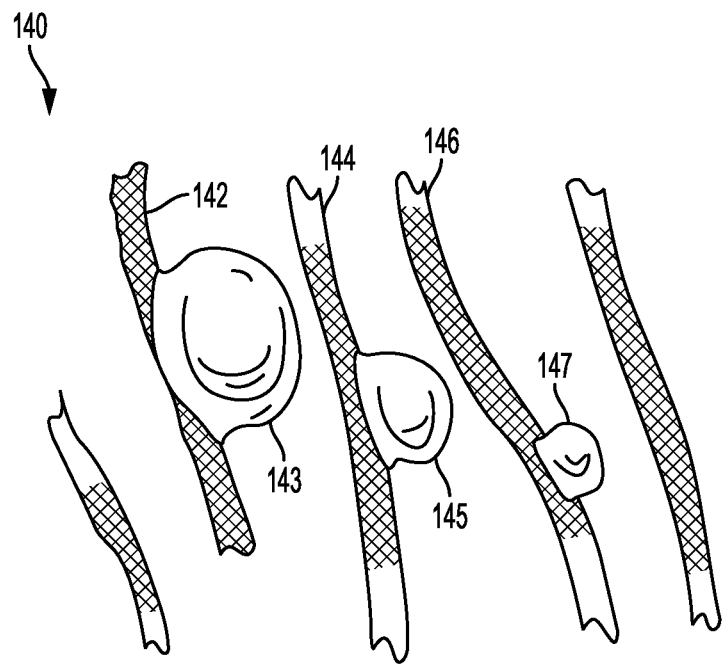
FIG. 20 is a graphical representation of an adjunct material including multiple fibers associated with vessels having at least one medicant disposed therein.
Figure 21:
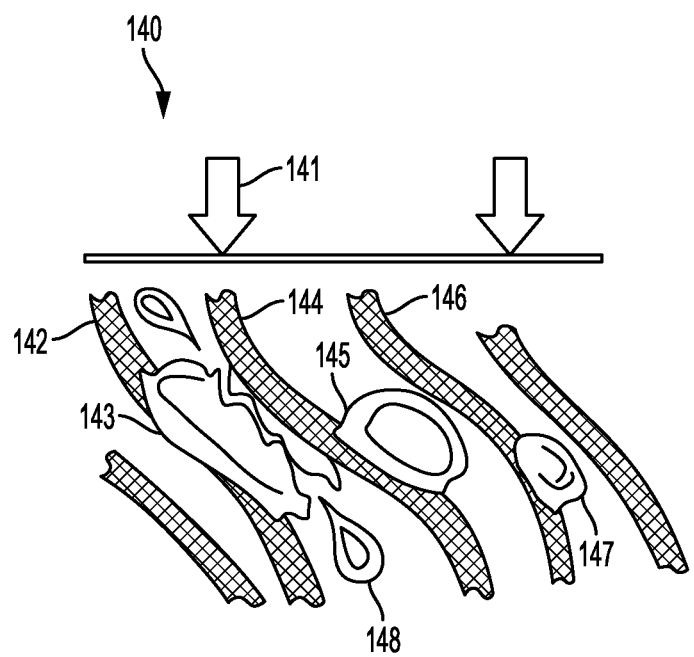
FIG. 21 is a graphical representation of the adjunct material of FIG. 20, showing the at least one medicant released from the adjunct material under the effect of strain.

FIG. 20 and FIG. 21 illustrate an adjunct 140 in the form of multiple fibers, three of which are denoted by way of example as fibers 142, 144, 146. As shown, each of the fibers 142, 144, 146 is associated with a respective one of vessels 143, 145, 147 retaining a medicant. The vessels 143, 145, 147 can retain the same or different medicants. In the illustrated example, the vessels 143, 145, 147 are in the form of irregularly shaped rounded beads having different sizes, however they can be shaped in any other manner and can have various sizes. The vessels can be applied to the fibers as a powder or they can be bonded, anchored to, or otherwise associated with the fiber strands. The vessels can remain associated with the fibers or they can be released from the fibers to thus deliver a desired treatment using the adjunct.

As shown in FIG. 21, when strain is applied to the adjunct 140, which is schematically shown by arrows 141, the fibers can deform and vessels can break and release the medicant incorporated therein. The magnitude of the strain can control rates of release of the medicants. For example, as shown in FIG. 21, the vessel 143 is broken and a medicant 148 is being released. In some aspects, the vessels can be broken at different times, depending on their size and/or other properties. In this example, the vessel 143 can be broken first to release the medicant 148 retained therein, as shown in FIG. 21, after which the smaller vessel 145 and then even smaller vessel 147 can break thus releasing respective medicants at different times (not shown). However, depending on the applied pressure and other factors, one or more vessels can break simultaneously. Furthermore, as mentioned above, the vessels 143, 145, 147 can absorb at different times so as to release the respective medicants at different times.

Figure 22:
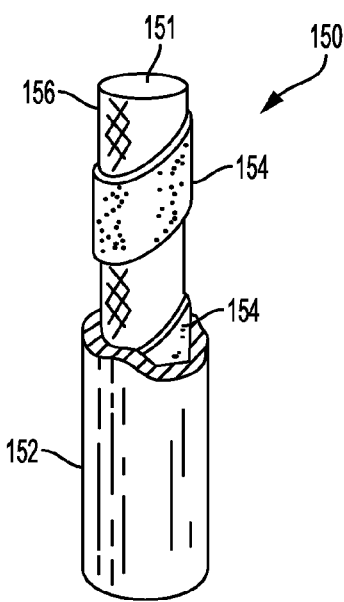
FIG. 22 is a graphical representation of an adjunct material configured to release at least one medicant in response to strain applied to the adjunct material.

In some aspects, an adjunct can have various surface textures of its fibers and it can release one or more medicants in various ways to influence or control re-growth of tissue. The adjunct can be delivered by staples carrying the adjunct thereon such that the medicants release when the staple is deformed upon staple deployment. For example, FIG. 22 illustrates an adjunct 150 having an outer layer or coating 152 encapsulating an inner layer 154 disposed over a staple 151 of a surgical device used to deliver the adjunct 150. However, in some aspects, rather than being disposed over a staple, the adjunct 150 can be disposed over a fiber lattice which can be folded into a tubular or other shape.

Figure 23:
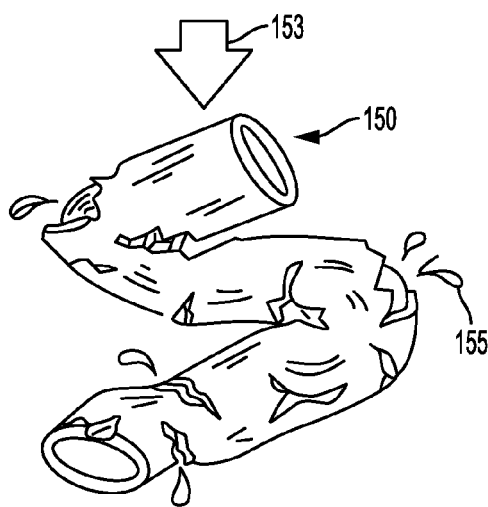
FIG. 23 is a graphical representation of the adjunct material of FIG. 22, showing the at least one medicant being released in response to strain applied to the adjunct material.

A first medicant can be retained between the outer coating 152 and the inner layer 154, and a second medicant can be incorporated into the inner layer 154. The inner layer 154 can be in the form of a flexible mesh wound over the fiber 156. When strain is applied to the adjunct 150 (e.g., when the staple 151 is deformed), as schematically shown by an arrow 153 in FIG. 23, the outer coating 152 can be caused to also deform and rupture. Upon the rupture of the outer coating 152, the first medicant retained between the outer coating 152 and the inner layer 154 can release (155) the first medicant as a bolus dose. The second medicant incorporated into the inner layer 154 can commence its release as a timed release after the first medicant is released or during the time when the first medicant is released. The release of the second medicant to tissue can be regulated by the release of the first medicant. The second medicant can alternatively be released at a bolus dose. It should be appreciated that the adjunct 150 can include one medicant disposed within the inner layer 154 that can release as a bolus dose.

Figure 24:
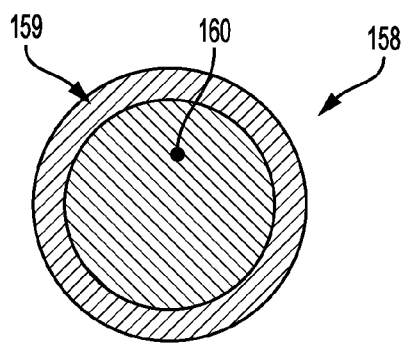
FIG. 24 is a graphical representation of a vessel having at least one medicant encapsulated therein.
Figure 25:
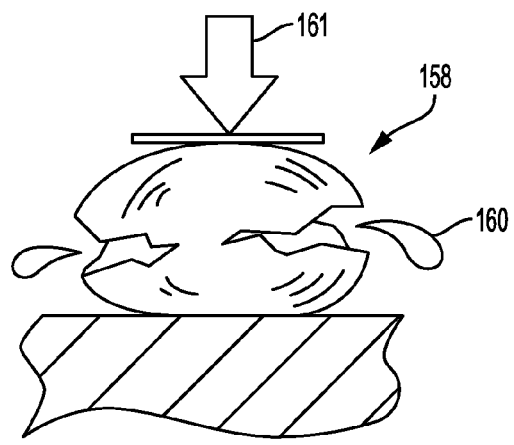
FIG. 25 is a graphical representation of the vessel of FIG. 24, showing the at least one medicant being released in response to strain applied to the vessel.

As mentioned above, an effective amount of at least one medicant disposed within or associated with an adjunct can be retained within distinct vessels carried by the adjunct. The vessels can be disposed within one or more regions of the adjunct or otherwise associated therewith. FIG. 24 and FIG. 25 illustrate an example of a vessel 158 in the form of a pellet or capsule having an outer coating 159 encapsulating therewithin at least one medicant 160. In this example, the vessel 158 has a spherical shape and resembles a gobstopper. However, it should be appreciated that the vessel can have any other shape. Furthermore, in some exemplary implementations, the outer coating 159 can encapsulate an inner region including at least one bioabsorbable polymer having at least one medicant incorporated therein. The vessels 158 can include multiple layers having different degradation rates and releasably retaining therein one or more medicants. Each of the layers can retain a different medicant, or two or more of the layers can carry the same medicant.

When a strain is applied to the vessel 158 as schematically shown by an arrow 161 in FIG. 25, the outer coating 159 can break or rupture such that its contents in the form of the at least one medicant 160 are released. Additionally or alternatively, the outer coating 159 can absorb, dissolve or otherwise disintegrate upon exposure of the vessel 158 to one or more environmental conditions such that the at least one medicant 160 is released from the vessel 158.

Figure 26:
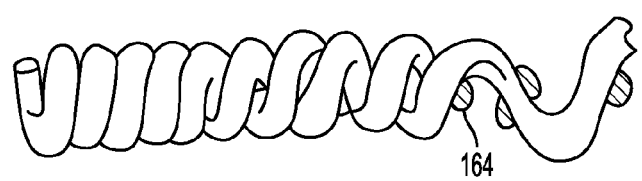
FIG. 26 is a graphical representation of an adjunct material configured to release at least one medicant when the adjunct material changes its conformation.
Figure 27:
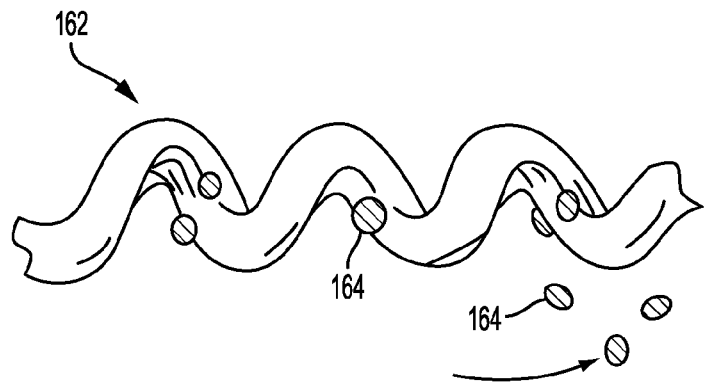
FIG. 27 is a graphical representation of the adjunct material of FIG. 26, showing the at least one medicant being released in response a change in the conformation of the adjunct material.

FIG. 26 and FIG. 27 illustrate an example of an adjunct 162 in the form of a fiber lattice having a certain conformation that is changeable, such as by the action of water and/or other agents that the adjunct is subjected to at the treatment site. As shown in FIG. 26, the adjunct 162 having a shape of a tightly wound spiral can retain therein one or more vessels carrying a medicant 164. The medicant 164 can be retained in association with the adjunct 162 by being held tightly by fibers of the adjunct. For example, the medicant can include a multilayered medicant/absorbable polymer structure where an outermost one of the layers includes an absorbable polymer that can be bound to the fibers of the adjunct, e.g., bonding of one absorbable polymer to another absorbable polymer, as will be appreciated by a person skilled in the art.

When the adjunct 162 is delivered at the treatment site, the wound fibers thereof can swell and increase in length, or elongate, such that the distances between the fibers increase and the adjunct 162 "unwinds" and releases the medicant 164 "trapped" within the adjunct 162, as shown in FIG. 27. The fibers of the adjunct 162 can unwind such that the entire adjunct 162 adopts a different conformation, like in the example of FIG. 26 and FIG. 27. However, in some aspects, the fibers of the adjunct can begin to unwind or fray from an end or other surface of the adjunct.

Figure 28:
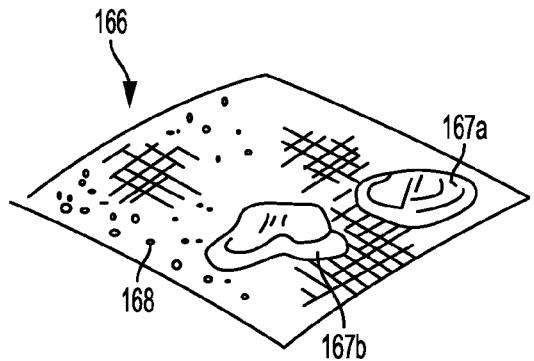
FIG. 28 is another graphical representation of an adjunct material configured to release at least one medicant when the adjunct material changes its conformation.
Figure 29:
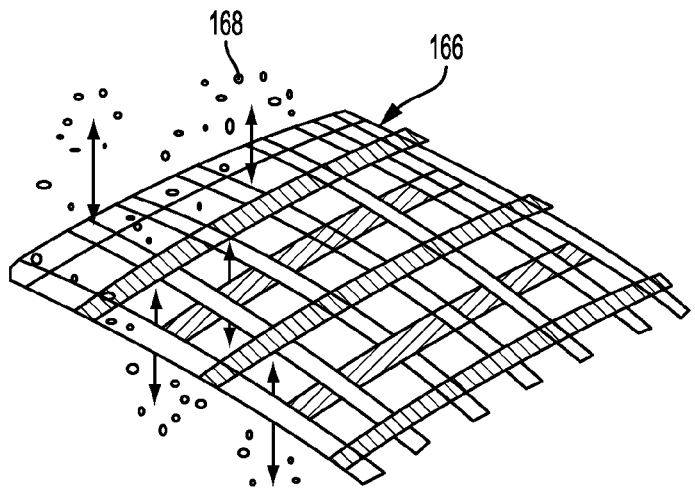
FIG. 29 is a graphical representation of the adjunct material of FIG. 28, showing the at least one medicant being released in response a change in the conformation of the adjunct material.

FIG. 28 and FIG. 29 illustrate another example of an adjunct 166 having a medicant 168 releasably retained therein. In this example, the adjunct 166 is in the form of a sheet-like fiber woven mesh. As shown in FIG. 28, the tight fibers of the adjunct 166 in its original configuration allow the medicant 168 to be retained therein. When the adjunct 166 is delivered at the treatment site, water and/or other agents, shown schematically as drops 167a, 167b in FIG. 28, can cause the fibers to swell and elongate such that the distances between the fibers increase, as shown in FIG. 29. In this way, the medicant 168 is released, as also shown in FIG. 29. A person skilled in the art will appreciate that the adjunct 166 can be formed from different types of fibers. The fibers can have different absorption rates, density, direction, patterns, size, and other properties that are selected so as to provide desired tissue re-growth. While some regions of the adjunct can be configured to release at least one medicant so as to encourage tissue re-growth, one or more regions of the adjunct can be configured to release at least one medicant so as to discourage tissue re-growth.

In aspects in which at least one medicant is disposed within a vessel formed from a bioabsorbable polymer coating encapsulating the medicant, the medicant can be configured to be released from the vessel at certain time based on various factors. The factors can include, for example, a degradation rate of the bioabsorbable polymer, a volume of the vessel, a surface area of the vessel, environmental conditions in a physiological environment surrounding the vessel and responsiveness of the bioabsorbable polymer to such conditions, a number of layers of the bioabsorbable polymer, a concentration of the medicant, and a type of association between the medicant and the bioabsorbable polymer.

Figure 30:
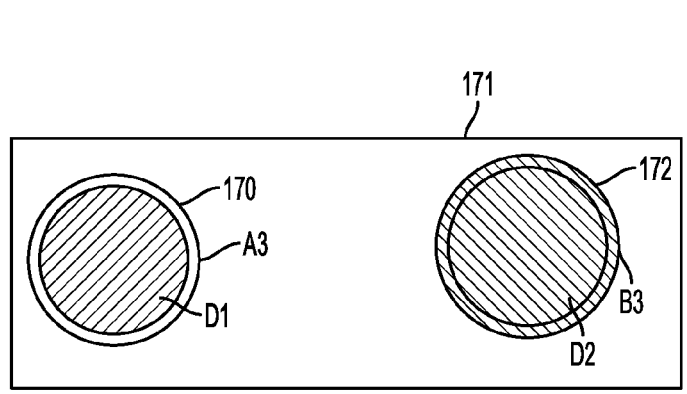
FIG. 30 is a graphical representation of an adjunct material having vessels configured to release at least one medicant encapsulated therein in a non-homogeneous manner.

FIG. 30 illustrates an example of first and second vessels 170, 172 that can be associated with a schematically shown adjunct 171. In this example, the first and second vessels 170, 172 are in the form of spherical beads. However, other types of vessels can be used additionally or alternatively such that the adjunct 171 can include one or more different types of vessels carrying different types of medicants. The first and second vessels 170, 172 have absorbable polymer outer coatings A3, B3 that have different degradation rates which therefore control release of first and second medicants D1, D2 encapsulated within the coatings A3, B3 in different manners. A degradation rate of the outer coating A3 can be higher than a degradation rate of the outer coating B3. Thus, the first medicant D1 is released from the first vessel 170 before the second medicant D2 is released from the second vessel 172. For example, the first medicant D1 can be an inflammatory agent that is released within 1-2 days after the adjunct 171 is delivered to a treatment site. The second medicant D2 can be an anti-inflammatory agent that is released within 3-5 days after the delivery of the adjunct 171. In this way, the release of the medicants D1, D2 from the first and second vessels 170, 172 can provide a desired effect on tissue in-growth.

Figure 31:
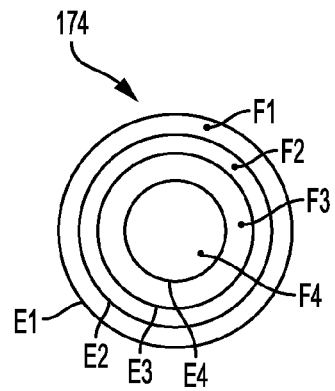
FIG. 31 is a graphical representation of a vessel configured to release multiple medicants encapsulated at different layers thereof in a non-homogeneous manner.

A vessel having at least one medicant encapsulated therein can have multiple medicants associated therewith in a number of different ways. FIG. 31 illustrates an example of a vessel 174 in a form of a sphere having multiple concentric layers each carrying a respective at least one medicant. In this example, as shown in FIG. 31, the vessel 174 has, from the outside to the inside, four distinct layers E1, E2, E3, E4 having first, second, third, and fourth medicants F1, F2, F3, F4, respectively. Each of the layers E1, E2, E3, E4 can have different degradation rate, thickness, density, responsiveness to environmental conditions, and other properties that control release of the medicants disposed therein. For example, the outermost first layer E1 can be configured to degrade first such the medicant is released first, and the other layers E2, E3, E4 can be configured to degrade such that an outer layer degrades before an inner layer does.

As each layer degrades, a respective medicant incorporated therein is released. It should be appreciated that the layers can be selected such that at least one inner layer can start to degrade after only a portion of at least one outer layer has been degraded. The medicants F1, F2, F3, F4 disposed within the multi-layer vessel 174 can be different or at least some of the medicants can be the same. The medicants can be released as a bolus dose or in other manners. For example, the first medicant F1 disposed within the first layer E1 can be released as a bolus dose substantially immediately upon delivery of an adjunct retaining the vessel 174 to tissue. Release of the second medicant F2 disposed within the second layer E2 can be regulated by the release of the first medicant F1.

A spatial distribution of medicants in an adjunct can vary depending on a type of the medicants and a desired effect on tissue in-growth. Targeted delivery of the medicants can be accomplished in a number of ways. For example, an adjunct can be configured to release one or more medicants in a heterogeneous manner such that various medicants can be delivered to tissue at different times, to facilitate desired healing. Different portions of the adjunct can be formed from different materials or form the same material treated so as to have different absorption rates.

Figure 32:
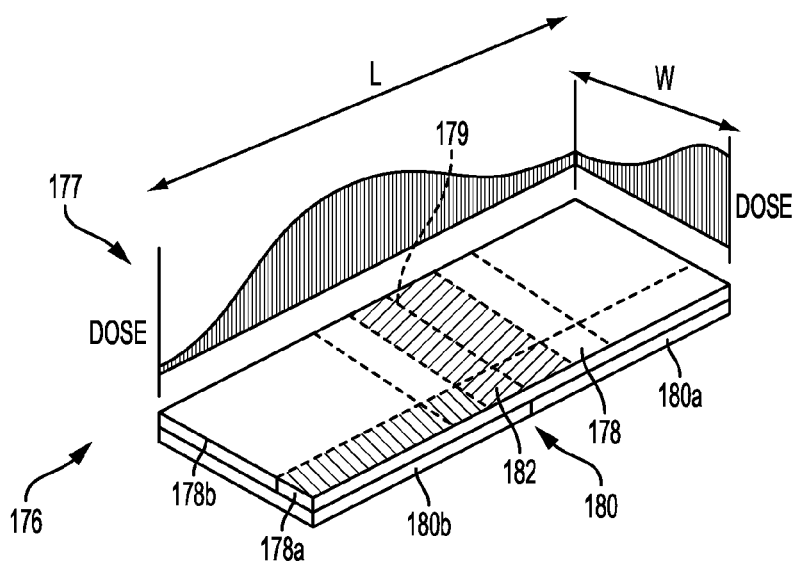
FIG. 32 is a graphical representation of an adjunct material having different portions configured to release at least one medicant in a non-homogeneous manner.

FIG. 32 illustrates an adjunct 176 in the form of a laminate including heterogeneous portions or layers having different degradation rates and incorporating different medicants. As shown, the adjunct 176 has a top layer or portion 178 and a bottom layer or portion 180 that have different degradation rates. Furthermore, each of the top and bottom portions 178, 180 can have various portions having degradation rates that vary in a distinct or continuous manner. The degradation rates can vary across the adjunct in a number of suitable ways that depend on a desired treatment effect to be provided by the adjunct.

In the example of FIG. 32, the top portion 178 of the adjunct 176 has two portions 178a, 178b having different degradation rates. The bottom portion 180 has two portions 180a, 180b having different degradation rates. Each of the portions can include a different medicant such that, as a portion degrades, a respective medicant is eluted or released. The degradation rates and distribution of the medicants within one or more of the portions 178a, 178b, 180a, 180b can further vary in a distinct or continuous manner such that the adjunct 176 can provide an elution profile shown in a graph 177 in FIG. 32. As shown, a central area 182 of the adjunct 176 centered around a mid-portion 179 thereof has an increased elution rate of one or more medicants that peaks at the mid-portion 179, whereas smaller amount of the medicant(s) is eluted from opposite sides of the adjunct 176 along its length L. The increased elution rate can be due to properties of the adjunct 176 at the central area 182 and the concentration of the medicants.

As further shown in FIG. 32, the adjunct 176 is configured to release medicants in different elution profiles along the length L thereof and along a width W thereof. For example, the medicants can be released along the width W as a bolus dose and along the length as a time-release dose. Release of one or more of the medicants can regulate release of at least one other of the medicants. However, the medicants can be released in any other manner, depending on a desired treatment to be delivered.

Figure 33:
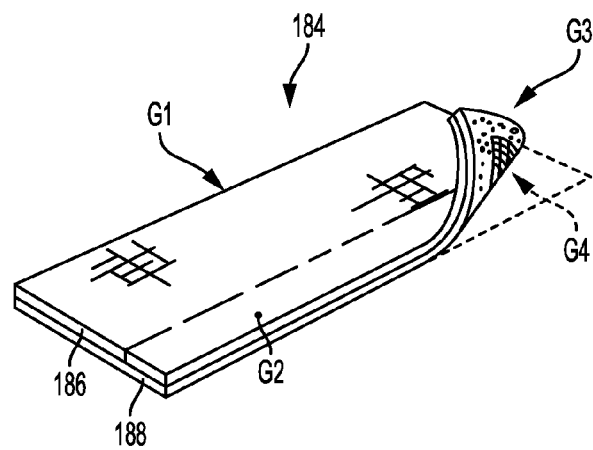
FIG. 33 is another graphical representation of an adjunct material having different portions configured to release at least one medicant in a non-homogeneous manner.
Figure 34:
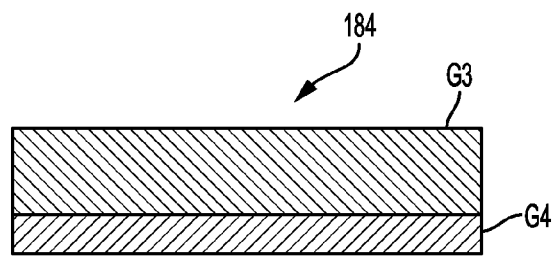
FIG. 34 is a graphical representation of a side view of the adjunct material of FIG. 33.

FIG. 33 illustrates another example of an adjunct 184 having top and bottom layers or portions 186, 188. Similar to the adjunct 176 in FIG. 32, each of the top and bottom portions 186, 188 of the adjunct 184 can have different medicants disposed therein. Thus, as shown in FIG. 33, the top portion 186 can have first and second medicants G1 and G2, at respective portions thereof. The bottom portion 188 can have third and fourth medicants G3 and G4 at respective portions thereof disposed such that the third medicant G3 is in a portion disposed over a portion carrying the fourth medicant G4, as also shown in FIG. 34.

Figure 35:
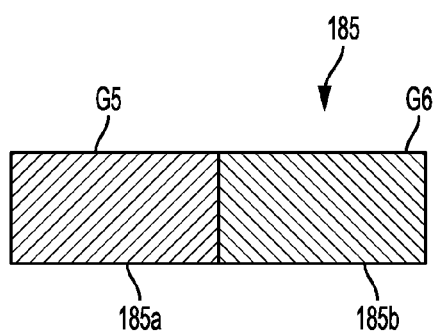
FIG. 35 is a graphical representation of a side view of an adjunct material having different portions configured to release at least one medicant in a non-homogeneous manner.
Figure 36:
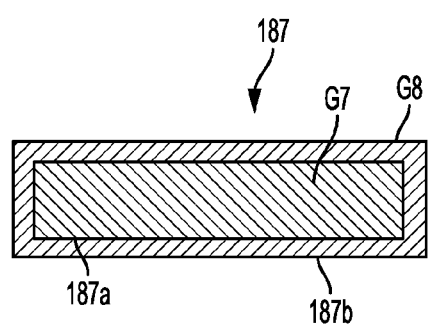
FIG. 36 is another graphical representation of a side view of an adjunct material having different portions configured to release at least one medicant in a non-homogeneous manner.

FIG. 35 illustrates an example of a portion of an adjunct 185 that can be similar to adjunct 176 (FIG. 32) or adjunct 184 (FIG. 33). As shown in FIG. 35, the adjunct 185 can have side-to-side portions 185a, 185b having different medicants G5, G6 disposed therein. FIG. 36 illustrates another example of a portion of an adjunct 187 having an inner portion 187a and an outer portion 187b having different medicants G7, G8 disposed therein.

In some aspects, elution rates of at least one medicant from an adjunct having one or more distinct portions formed from at least one bioabsorbable polymer can depend on a position of the portions within the adjunct, a degradation rate of the at least one bioabsorbable polymer, responsiveness of the at least one bioabsorbable polymer to environmental conditions, and an overall configuration of the adjunct.

Figure 37:
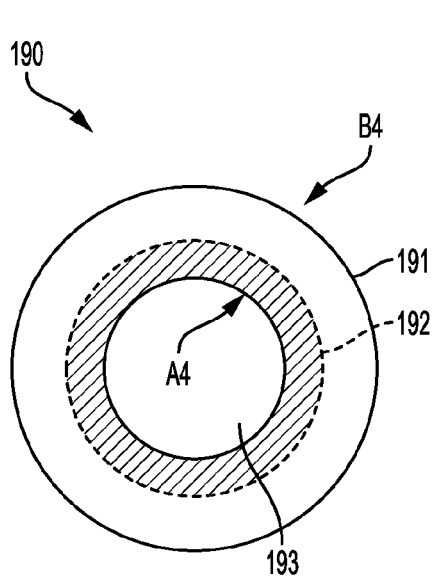
FIG. 37 is a graphical representation of an adjunct material having different concentric regions configured to release at least one medicant at different rates.

FIG. 37 illustrates an example of an adjunct 190 in a form of a cylinder that has outer and inner concentric layers 191, 192 which can be formed from different types of absorbable polymer and can have different thickness and other properties. The outer and inner layers 191, 192 can have different medicants B4, A4 disposed therein and that can be released from the respective layers 191, 192 at different times and at different rates. In this example, an innermost cavity 193 lined by the inner layer 192 can be empty. The medicant A4 can be configured to commence to release before the medicant B4 is released. It should be appreciated that, in some aspects, the outer and inner layers 191, 192 can be disposed over a fiber.

Figure 38:
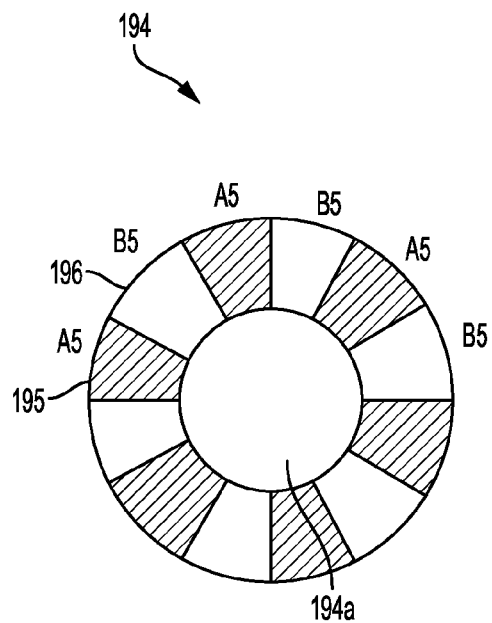
FIG. 38 is a graphical representation of an adjunct material having different radial regions configured to release at least one medicant at different rates.

FIG. 38 illustrates an example of a tubular adjunct 194 that has multiple radial portions formed from different types of absorbable polymer. As shown, the adjunct 194 has an inner cavity 194a having the radial portions disposed concentrically therearound. In the example illustrated, the portions can be formed from first and second types of polymer in an alternating manner, as shown by portions 195, 196 in FIG. 38 formed from the first and second polymers, respectively. The portion 195 formed from the first polymer has a medicant A5 disposed therein, the portion 197 formed from the second polymer has a medicant B5 disposed therein, and other portions formed from the first and second polymers have the medicants A5, B5 disposed therein in the same alternating manner, as shown in FIG. 38. Similar to the examples before, the medicants A5, B5 can be released from the respective layers at different times and at different rates. For example, the medicant A5 can be configured to commence to release before the medicant B5 is released.

Figure 39:
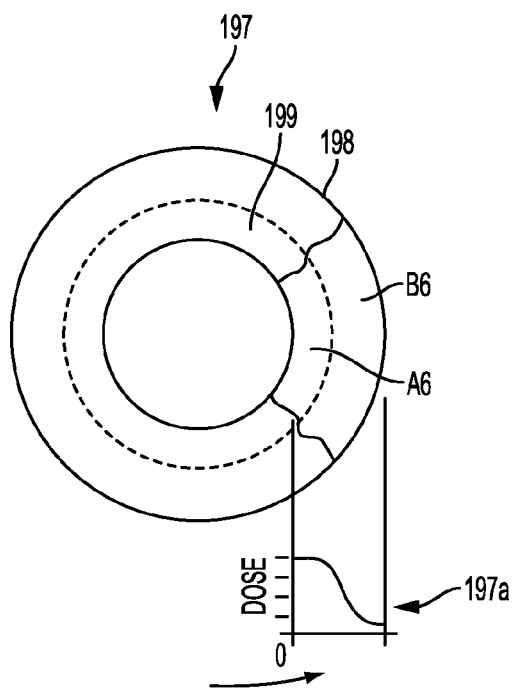
FIG. 39 is another graphical representation of an adjunct material having different concentric regions configured to release at least one medicant at different rates.

FIG. 39 illustrates an example of a tubular adjunct 197 similar to adjunct 190 (FIG. 37). As shown in FIG. 39, the adjunct 197 has outer and inner concentric layers 198, 199 which can be formed from different types of absorbable polymer and can have different thickness and other properties. The outer and inner layers 198, 199 can have different medicants B6, A6 disposed therein and that can be released from the respective layers 198, 199 at different times and at different rates. For example, as shown in a graph 197a in FIG. 39, the medicant A6 can release before the medicant B6 is released. Furthermore, the medicant A6 can release at a higher dosage than the medicant B6, as also shown in the graph 197a.

In at least some implementations, a staple cartridge can include a lubricant (e.g., sodium stearate or other lubricant) applied thereto that includes at least one medicant (e.g., LAE, Doxycycline, and/or other antimicrobial agent) releasable therefrom. The lubricant can be applied to the staple cartridge as a spray and can coat the cartridge and the staples releasably disposed therein. The lubricant including one or more medicants may allow the medicant(s) to be applied to the staples. In this way, the medicant(s) may be delivered to a targeted area (e.g., along a staple line defined by the staples) where the medicant(s) may be best able to facilitate wound healing, as discussed herein. The lubricant including one or more medicants can be used with an adjunct including one or more medicants, which may facilitate targeted wound healing.

Wound Healing

During performance of a surgical procedure, tissue of a patient can be wounded (e.g., cut, torn, punctured, etc.) in any of a variety of ways. The wounding may be an intended aspect of the surgical procedure, such as in an anastomosis procedure and/or when tissue is cut and fastened using a surgical device such as a surgical stapler. The wounded tissue typically heals over time in generally the same way for all patients.

Wound healing is traditionally considered to include four stages: hemostasis, inflammation, proliferation, and remodeling. The hemostasis stage generally involves blood clotting, e.g., stopping bleeding. In general, damaged blood vessels constrict to slow blood flow, platelets aggregate to help seal the wound site, the platelets activate fibrin to further facilitate wound sealing, and a blood clot forms at the wound site. The inflammation stage generally involves cleaning of the wound site. In general, the immune system provides a response to the threat of possible infection at the wound site via signaling to defensive immune cells such as neutrophils and macrophages. The proliferation stage generally involves rebuilding tissue with tissue growth and angiogenesis (blood vessel growth). In general, fibroblasts arrive at the wound site, the fibroblasts lay down collagen, the fibroblasts release growth factors that attract epithelial cells, and the epithelial cells attract endothelial cells. The remodeling stage, also referred to as a maturation stage, generally involves strengthening scar tissue at the wound site. In general, collagen fibers align and crosslink, and the scar matures to eventually fade away. Each of these four stages is discussed further below.

While each of wound healing's four stages involves a different aspect of the healing process, stages typically overlap with one another. Namely, each of the last three stages typically overlaps with its preceding stage, e.g., inflammation overlaps with hemostasis, proliferation overlaps with inflammation, and remodeling overlaps with proliferation. The speed at which the transition between stages occurs generally affects the speed of overall wound healing and thus generally affects patient recovery time, chances of complications arising, and/or patient comfort. Similarly, the length of each of the four individual stages generally affects the speed of overall wound healing and the patient's general recovery. In general, the slower the wound healing process, and in particular the longer it takes to begin the remodeling stage, the more likely that the wound will become infected, cause the patient discomfort, become a chronic wound, cause an ulcer, and/or develop pathological scarring.

The hemostasis stage generally begins within minutes of the initial injury, unless there are underlying clotting disorders, in which case hemostasis may be delayed. The hemostasis stage typically lasts for 30 to 60 minutes before the inflammation stage begins (e.g., before neutrophils arrive, as discussed below) and typically ends hours after the injury, e.g., 2 to 6 hours post-injury. Poor hemostatic control that results in a longer hemostasis stage can lead to increased bleeding and tissue damage. Additionally, a prolonged hemostasis stage can result in additional scar formation that delays the proliferation and remodeling stages.

In the hemostasis stage, injured blood vessels at the wound site are sealed. The blood vessels constrict in response to injury, e.g., in response to being cut, but this spasm ultimately relaxes. Blood platelets secrete vasoconstrictive substances to aid in this process. The platelets also form a stable clot sealing the damaged vessels. Under the influence of adenosine diphosphate (ADP) leaking from the damaged tissue at the wound site, the blood platelets aggregate and adhere to exposed collagen. The blood platelets secrete factors, which interact with and stimulate an intrinsic clotting cascade through the production of thrombin, which in turn initiates the formation of fibrin from fibrinogen. The clotting cascade occurs to achieve hemostasis, or stop blood loss by way of a fibrin clot. More particularly, the fibrin forms a mesh that strengthens the platelet aggregate into a stable hemostatic plug or clot, thereby reducing and/or preventing bleeding. The mesh serves as a scaffold for invading cells, such as neutrophils, macrophages, fibroblasts, and endothelial cells, during the inflammation and proliferation stages. Additionally, the platelets secrete various soluble factors, such as chemokines, cytokines, and platelet-derived growth factor (PDGF). This secretion generally initiates the inflammation stage of wound healing, as the soluble factors attract cells that phagocytize material (e.g., debris, microorganisms such as bacteria, and damaged tissue).

The clotting cascade occurs in the hemostasis stage just before the inflammatory stage begins. The inflammation stage typically begins within an hour of the injury and typically lasts for 2 to 6 days but can last even longer, e.g., up to 10 days. The longer the inflammation stage, the more likely that additional scarring will occur, thereby delaying the proliferation and remodeling stages. During the inflammation stage, the wounded tissue can show various signs of inflammation, such as erythema, heat, edema, pain, and functional disturbance. These signs can last for most or all of the inflammation stage. Accordingly, the longer the inflammation stage, the longer the tissue experiences these adverse effects of inflammation, which in turn can prolong patient discomfort and/or prolong the period of time in which the patient is particularly susceptible to infection. The adverse effects of inflammation can be severe enough in some patients to cause death. Inflammation must occur during proper wound healing, however, and its adverse effects tolerated in order for the final stages of wound healing to commence.

In the inflammation stage, the cells attracted by the soluble factors secreted in the hemostasis stage phagocytize material. Namely, immune cells including phagocytic cells, neutrophils, and macrophages destroy material in an effort to help prevent infection. The arrival of neutrophils generally signals the start of the inflammation stage. Neutrophils typically arrive at the wound site within an hour of wounding. The neutrophils are able to phagocytize debris and microorganisms and provide a first line of defense against infection. They are aided by local mast cells. Fibrin is broken down, and the degradation products attract macrophages. Macrophages typically appear 1 to 2 days post-injury. The macrophages are able to phagocytize bacteria and provide a second line of defense against infection. The macrophages secrete a variety of chemotactic factors and growth factors such as fibroblast growth factor (FGF), epidermal growth factor (EGF), transforming growth factor beta (TGF-β), and interleukin-1 (IL-1), which are traditionally recognized as directing the subsequent proliferation and remodeling stages. In other words, the macrophages release angiogenic substances to help begin the proliferation stage to stimulate capillary growth and granulation, thereby setting the stage for the remodeling stage. Lymphocytes (e.g., T lymphocytes) attracted to the wound site typically appear at the wound site after the macrophages appear.

The proliferation stage typically begins 2 to 5 days post-injury and typically lasts for 2 to 21 days. In the proliferation stage, the macrophages' secretion induces the proliferation of fibroblasts. The fibroblasts enter the wound site and form an extracellular matrix (ECM) by excreting collagen and fibronectin. The wound is thus "rebuilt" with new granulation tissue that includes the collagen and the ECM into which a new network of blood vessels develop, a process traditionally known as angiogenesis. The collagen increases the strength of the wound. Accordingly, the sooner collagen can be produced, e.g., the sooner that fibroblasts enter the wound area, the sooner the wound can gain strength and thereby be less likely to cause any number of problems such as infection and patient discomfort.

Concurrent with the ECM formation, epithelial cells (e.g., keratinocytes) migrate from the wound's edge to cover the wound and form a barrier between the wound and its environment. In other words, the epithelial cells resurface the wound, in a process traditionally known as epithelialization. The epithelial cells migrate over the granulation tissue but underneath the scab on the wound (if a scar was earlier formed). The epithelial cells must dissolve the clot, debris, and parts of the ECM in order to properly migrate over the wound. To facilitate their migration, the epithelial cells secrete a plasminogen activator, which activates plasminogen, turning it into plasmin to dissolve the clot, debris, and parts of the ECM. Additionally, since cells can only migrate over living tissue, the epithelial cells excrete collagenases and proteases such as matrix metalloproteinases (MMPs) to dissolve damaged parts of the ECM in their migrational path. In the final phase of epithelialization, contraction of the wound occurs as the fibroblasts differentiate into myofibroblasts to form the protective outer layer, or stratum corneum. Contraction can last for days or several weeks and continues even after the wound is completely reepithelialized. Contraction is the main cause of scarring associated with wound healing.

The remodeling stage generally begins when the levels of collagen production and degradation equalize. In other words, remodeling generally begins once a scar has formed and the tensile strength of the wound has begun to increase. The remodeling stage typically begins 7 to 21 days post-injury and typically lasts for at least 3 weeks and can last for months or years depending on factors such as wound size and re-injury.

In the remodeling stage, the wound matures to become stronger, e.g., to have increased tensile strength. In general, weaker type III collagen, which is common at the wound site in the proliferation stage, is replaced by stronger type I collagen. This replacement generally involves reorganizing, crosslinking, and aligning the temporary collagen fibers. As remodeling progresses, the scar disappears.

Figure 40:
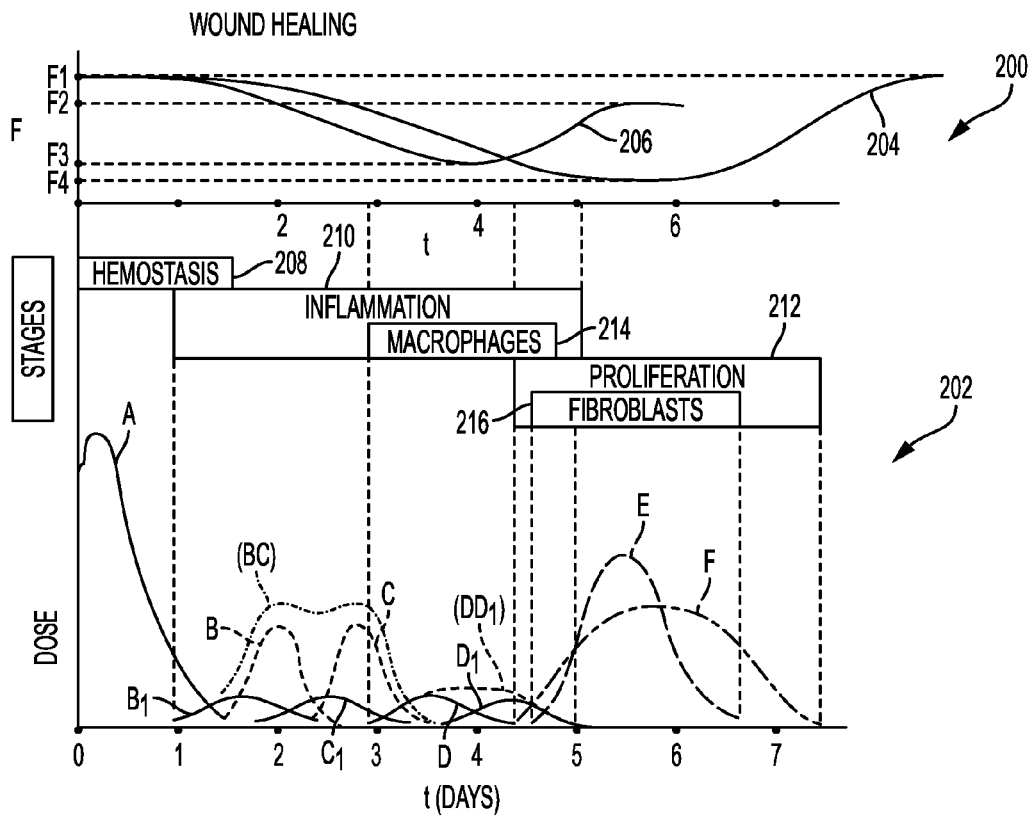
FIG. 40 is a graphical representation of an embodiment of wound healing over time with doses of medicants.

FIG. 40 illustrates a depiction of wound healing over time. An upper portion of FIG. 40 shows a first wound healing graph 200 of tissue strength (tensile force F) versus time (t). A lower portion of FIG. 40 shows a second wound healing graph 202 of medicant dose amount versus time (t). The first and second graphs 200, 202 are plotted with a shared horizontal axis to facilitate comparison of data shown in the first and second graphs 200, 202. Time zero (t=0) in the first and second graphs 200, 202 represents a time of injury, e.g., when a wound occurs. A first tissue strength F1 in the first graph 200 thus represents the tissue's strength at the wound at the time of injury.

The first graph 200 includes a first curve 204 of tissue strength over time during typical wound healing, and includes a second curve 206 of tissue strength over time during accelerated wound healing in accordance with at least some methods, systems, and devices provided herein. The second curve 206 of accelerated wound healing can be achieved using one or more doses of medicants provided in the second graph 202, as discussed further below. Stages of wound healing (a hemostasis stage 208, an inflammation stage 210, and a proliferation stage 212) are shown in FIG. 40 with reference to the second graph 202, and hence also to the second curve 206 of the first graph 200. The first curve 204 in the first graph 200 has a different timing of hemostasis, inflammation, and proliferation stages, as discussed below.

The time scale in FIG. 40 is an example only. As discussed above, the timing of wound healing can vary, e.g., the stages of wound healing can begin at different times for different wounds and/or for different patients. FIG. 40 demonstrates that for the same wound in the same patient, the wound's typical healing, as illustrated by the first curve 204, is improved when one or more medicants are dosed to the patient in accordance with the second graph 202, as illustrated by the second curve 206. In other words, regardless of the time scale of the horizontal axis of the first and second graphs 200, 202, the dosing of one or more medicants may provide for faster wound healing than typical wound healing and may provide a shorter period of minimum tissue tensile strength than typical wound healing.

As demonstrated by the first curve 204, typical wound healing involves the tissue having the first tissue strength F1 at time zero and decreasing in strength over time to a minimum tissue strength F4 that begins during day four (5>t>4) during an inflammation stage and persists until sometime during day six (7>t>6) before tissue strength begins to gradually improve back toward the first tissue strength F1. The first tissue strength F1 can be re-achieved during typical wound healing, as shown by the first curve 204, at some point during or after a proliferation stage. The tissue's strength begins to decrease from the first tissue strength F1 in response to inflammation, e.g., in response to entry into the inflammation stage, during day one (2>t>1) and continues decreasing toward and/or remains at its lowest level F4 until inflammation of the tissue begins to subside, e.g., until the proliferation stage begins, during day six. The tissue is thus decreasing in strength and is at its most vulnerable to succumb to any number of inflammation's adverse effects for a relatively long period of time that starts during day one and lasts into day six.

As demonstrated by the second curve 206, accelerated wound healing in accordance with at least some embodiments of the methods, systems, and devices provided herein involves the tissue having the first tissue strength F1 at time zero and decreasing in strength over time to a minimum tissue strength F3 that begins during day three (4>t>3) during the inflammation stage 210 and persists until sometime during day four (5>t>4) before tissue strength begins to gradually improve back toward the first tissue strength F1. The minimum tissue strength F3 in the accelerated wound healing is greater than the minimum tissue strength F4 in the typical wound healing. The tissue experiencing the accelerated wound healing thus never has strength as low as that during typical wound healing. In other words, the accelerated wound healing allows for less tissue weakening than typical wound healing. The tissue's strength begins to decrease from the first tissue strength F1 in response to inflammation, e.g., in response to entry into the inflammation stage 210, during day one (2>t>1) and continues decreasing toward and/or remains at its lowest level F3 until inflammation begins to improve, e.g., until the proliferation stage 212 begins, during day four. The tissue is thus decreasing in strength and is at its most vulnerable to succumb to any number of inflammation's adverse effects sooner and for a shorter period of time than typical wound healing, i.e., starting during day one and lasting into day four instead of starting during day one and lasting into day six. In other words, the accelerated wound healing can provide for a shorter inflammation stage than typical wound healing. The tissue's strength may not increase back to its pre-wound tissue strength F1 after the inflammation stage 210 in the accelerated healing but can increase to a level close thereto, as shown by the second curve 206 reaching a new maximum tissue strength F2 during the proliferation stage 212.

Figure 41:
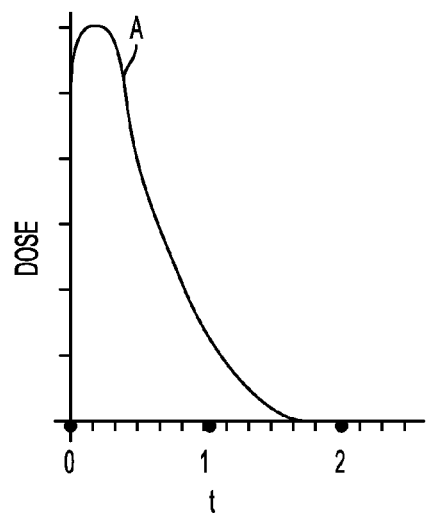
FIG. 41 is a graphical representation of a hemostatic stage in the wound healing of FIG. 40.
Figure 42:
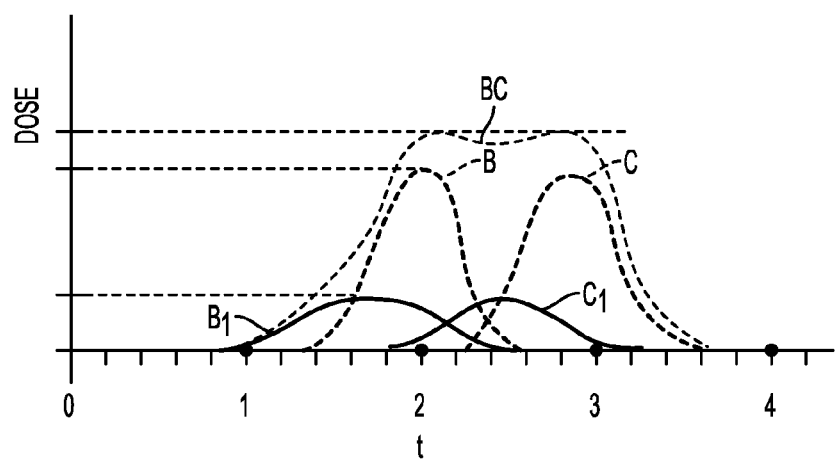
FIG. 42 is a graphical representation of a portion of an inflammation stage in the wound healing of FIG. 40.
Figure 43:
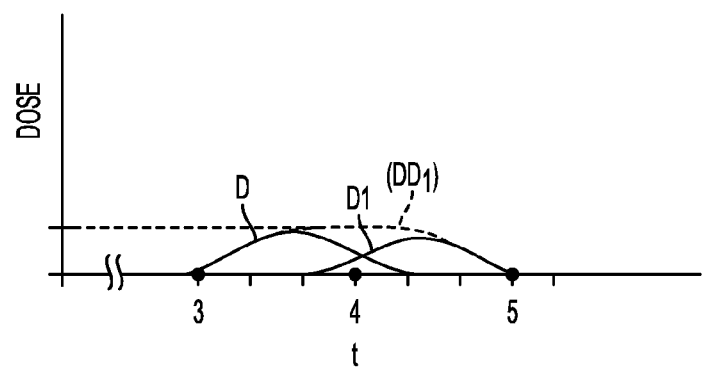
FIG. 43 is a graphical representation of another portion of the inflammation stage in the wound healing of FIG. 40.
Figure 44:
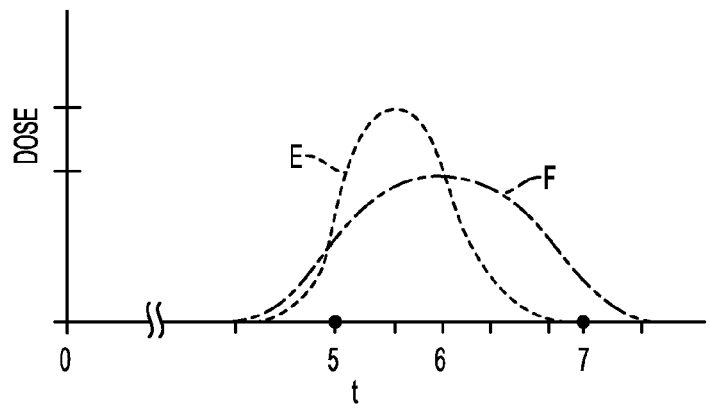
FIG. 44 is a graphical representation of a proliferation stage in the wound healing of FIG. 40.

The second graph 202 illustrates an example of doses of medicants that can be administered to the patient to achieve the accelerated wound healing indicated by the second curve 206. The doses of medicants can include a dose of medicant A configured to facilitate hemostasis in the hemostasis stage 208 as also shown in FIG. 41; doses of medicant B, medicant $B_1$, medicant C, and medicant $C_1$ configured to facilitate inflammation in the inflammation stage 210 as also shown in FIG. 42; doses of medicant D and medicant $D_1$ configured to inhibit MMPs during a macrophages phase 214 of the inflammation stage 210 (e.g., during a time when macrophages are present and active at the wound site in the inflammation stage 210) as also shown in FIG. 43; a dose of medicant E configured to prevent inflammation in the proliferation stage 212 during a fibroblasts phase 216 of the proliferation stage 212 (e.g., during a time when fibroblasts are present and active at the wound site in the proliferation stage 212) as also shown in FIG. 44; and a dose of medicant F configured to facilitate tissue growth in the proliferation stage 212 during a fibroblasts phase 216 of the proliferation stage 212 (e.g., during a time when fibroblasts are present and active at the wound site in the proliferation stage 212) as also shown in FIG. 44. Each of the medicants A, B, $B_1$, C, $C_1$, D, $D_1$, E, F is discussed further below.

In one example, at least one medicant can be administered to tissue during each of the hemostasis, inflammation, and proliferation stages 208, 210, 212 of the wound healing to overall improve the wound healing process with all of the medicants shown in the second graph 202 being administered, e.g., the medicant A in the hemostasis stage 208, the medicants B, $B_1$, C, $C_1$, D, $D_1$ in the inflammation stage 210, and the medicants E, F in the proliferation stage 212. In another example, at least one medicant can be administered to tissue during each of the hemostasis, inflammation, and proliferation stages 208, 210, 212 of the wound healing to overall improve the wound healing process without all of the medicants shown in the second graph 202 being administered, e.g., the medicant A in the hemostasis stage 208, at least one of the medicants B, $B_1$, C, $C_1$, D, $D_1$ in the inflammation stage 210 (and in a further example, at least two of the medicants B, $B_1$, C, $C_1$, D, $D_1$), and one or both of the medicants E, F in the proliferation stage 212. The subset of the medicants A, B, $B_1$, C, $C_1$, D, $D_1$, E, F administered can be determined on a case-by-case basis based on any one or more factors such as wound type, wound size, surgeon preference, available medicants at a time of surgery, patient medical history, etc. In yet another example, at least one medicant can be administered to tissue during only one or two of the hemostasis, inflammation, and proliferation stages 208, 210, 212 to improve select stages of the wound healing process (with an improvement in one stage being able to improve subsequent stage(s) of the wound healing process, as discussed above) without all of the medicants shown in the second graph 202 being administered. Further, the medicants can be administered in the selected one or two stages as shown in the second graph 202 (e.g., the medicant A in the hemostasis stage, the medicants B, $B_1$, C, $C_1$, D, $D_1$ in the inflammation stage 210, the medicants E, F in the proliferation stage 212) or can be selectively administered in the selected one or two stages (e.g., the medicant A in the hemostasis stage 208, at least one of the medicants B, $B_1$, C, $C_1$, D, $D_1$ in the inflammation stage 210 (and in a further example, at least two of the medicants B, $B_1$, C, $C_1$, D, $D_1$), one or both of the medicants E, F in the proliferation stage 212). The one or two of the stages 208, 210, 212 in which medicant doses are administered can be determined on a case-by-case basis based on any one or more factors such as wound type, wound size, surgeon preference, available medicants at a time of surgery, patient medical history, etc.

As discussed herein, an adjunct material including one or more medicants releasable therefrom can be delivered to tissue, e.g., using a surgical stapler. The adjunct material's one or more medicants can include each of the medicants A, B, $B_1$, C, $C_1$, D, $D_1$, E, F being administered, whether it be all of the medicants A, B, $B_1$, C, $C_1$, D, $D_1$, E, F or a subset thereof. The administered ones of the medicants A, B, $B_1$, C, $C_1$, D, $D_1$, E, F can thus be delivered to the patient concurrent with a time of the injury (t=0). As discussed herein, the adjunct material's medicants can be releasable therefrom in a variety of ways. The timing of the release can allow the medicants to be administered to tissue at the appropriate time in the wound healing process, as also discussed herein. The medicants A, B, $B_1$, C, $C_1$, D, $D_1$, E, F (or the selected subset thereof) can thus be simultaneously delivered to the patient but can be released to the patient's tissue at different times and over time to achieve the desired effects.

The medicant A configured to facilitate hemostasis can have a variety of configurations. In general, the medicant A can include a hemostatic agent configured to promote hemostasis. The administration of the medicant A may thus help stop bleeding and help shorten a length of the hemostasis stage 208 and, accordingly, help the inflammation stage 210 begin sooner than in typical wound healing. Examples of the medicant A include fibrin and thrombin. Also, examples of hemostatic agents configured to promote hemostasis and delivery thereof are described in U.S. Pat. Pub. No. 2013/0149343 entitled "Hemostatic Bioabsorbable Device with Polyethylene Glycol Binder" filed Dec. 13, 2011, U.S. Pat. No. 8,383,147 entitled "Reinforced Absorbable Synthetic Matrix For Hemostatic Applications" filed Aug. 22, 2012, and U.S. Pat. No. 8,329,211 entitled "Reinforced Absorbable Multi-Layered Fabric For Hemostatic Applications" filed May 17, 2010, which are hereby incorporated by reference in their entireties.

The medicant A can be administered in a variety of ways. In one example, the medicant A can be administered from a vessel. The vessel can include a bioabsorbable or dissolvable coating, e.g., a saccharide coating, etc., surrounding the medicant A. The coating can be configured to bioabsorb/dissolve relatively quickly so as to be administered to the wounded tissue within minutes of the injury, e.g., within minutes of t=0. The medicant A's hemostatic effects can thus begin prior to the start of the inflammation stage 210. As shown in FIG. 40 and FIG. 41, the dose of the medicant A can decrease over time as the agent dissipates in the tissue/the patient's body.

The medicants B, $B_1$, C, $C_1$ configured to facilitate inflammation can each have a variety of configurations. In general, the medicants B, $B_1$, C, $C_1$ can each include an inflammatory agent configured to promote inflammation. The medicants B, $B_1$, C, $C_1$ may thus help speed up the inflammatory process and, accordingly, help shorten the inflammation stage 210 as compared to typical wound healing, help the proliferation stage 212 begin sooner than in typical wound healing, help the tissue reach its minimum strength F3 sooner than when the minimum strength F4 is reached in typical wound healing, and help shorten a period of time at which the tissue is at its minimum strength F3 as compared to typical wound healing. Examples of the medicants B, $B_1$, C, $C_1$ include pro-inflammatory medicants. In some aspects, the medicants B, $B_1$, C, $C_1$ can each include the same agent. In other aspects, the medicants B, $B_1$ can each include the same agent, and the medicants C, $C_1$ can each include the same agent as each other that is a different agent than the medicants B, $B_1$. In still other aspects, the medicants B, $B_1$, C, $C_1$ can each include a different agent from one another.

The medicants B, $B_1$, C, $C_1$ can each be administered in a variety of ways. In one example, the medicant B can be administered as a vessel with the medicant $B_1$ being a coating of the medicant B vessel, and the medicant C can be administered as another vessel with the medicant $C_1$ being a coating of the medicant C vessel. The dosages of the vessel medicants B, C can be greater than the dosages of the coating medicants $B_1$, $C_1$, as shown in FIG. 40 and FIG. 42, as vessel coatings typically include less substance than the vessel that they surround.

In one example, the medicant $B_1$ can be configured to begin release prior to the medicant B, which can be configured to begin release prior to the medicant $C_1$, which can be configured to begin release prior to the medicant C. The inflammatory medicants B, $B_1$, C, $C_1$ can thus be configured to be stagger-released with each medicants' dose peaking at a different time (e.g., at a different point along the time t axis of the second graph 202). The different peak dosages of the inflammatory medicants B, $B_1$, C, $C_1$ can allow the medicants B, $B_1$, C, $C_1$ to have a cumulative inflammatory dose, shown as "BC" in FIG. 40 and FIG. 42, greater than any of their individual doses. In other words, the peak dosages of the individual medicants B, $B_1$, C, $C_1$ can be timed to contribute to an overall inflammatory dose "BC" greater than can be achieved individually with their doses. The inflammatory dose "BC" can generally have the shape of a square wave, as also shown in FIG. 40 and FIG. 42.

The inflammatory medicants B, $B_1$, C, $C_1$ can be configured to each begin release prior to the release of the other medicants effective in the inflammation stage 210, the medicants D, $D_1$ configured to inhibit MMPs. In this way, the tissue at the wound site can be allowed to be inflamed and approach its minimum tensile strength F3 a short time before day three (t=3), at which time the macrophage phase 214 of the inflammation stage 210 generally begins and during which the medicants D, $D_1$ can be administered.

The medicants D, $D_1$ configured to inhibit MMPs can each have a variety of configurations. In general, the medicants D, $D_1$ can each include an agent configured to inhibit MMP, e.g., an MMP inhibitor. The medicants D, $D_1$ can thus help less MMP be released in the inflammation stage 210, thereby allowing less of the ECM to be destroyed in the inflammation stage 210. The tissue at the wound site may thus be less torn down while still allowing the inflammatory process and, accordingly, allow the tissue to have more strength than in the typical wound healing process, e.g., F3>F4. Examples of the medicants D, $D_1$ include tissue matrix degradation inhibitors that inhibit the action of MMPs and other proteases. In one example, the medicants D, $D_1$ each include the same agent, but the medicants D, $D_1$ can differ from one another in at least some examples.

The medicants D, $D_1$ can each be administered in a variety of ways. In one example, each of the medicants D, $D_1$ can be administered via vessel. Each of the two vessels can include a coating configured to facilitate release of the medicants D, $D_1$ at the appropriate time in the wound healing process, e.g., at a time after release of the inflammatory medicants B, $B_1$, C, $C_1$, such as sometime 4 to 7 days after the injury (4<t<7). Examples of the coating include a copolymer having 90% polyglycolide (also referred to as polyglycolic acid (PGA)) and 10% polylactide (also referred to as polyactic acid (PCA)), such as Vicryl Rapide.

In one example, the medicant D can be configured to begin release prior to the medicant $D_1$. The MMP-inhibiting medicants D, $D_1$ can thus be configured to be stagger-released with each medicants' dose peaking at a different time (e.g., at a different point along the time t axis of the second graph 202). The different peak dosages of the MMP-inhibiting medicants D, $D_1$ can allow the medicants D, $D_1$ to have a cumulative MMP-inhibiting dose, shown as "$DD_1$" in FIG. 40 and FIG. 43, greater than their individual doses. In other words, the peak dosages of the individual medicants D, $D_1$ can be timed to contribute to an overall MMP-inhibiting dose "$DD_1$" greater than can be achieved individually with their doses.

The MMP-inhibiting medicants D, $D_1$ can be configured to each begin release prior to the release of the medicants E, F. In this way, the tissue at the wound site can be allowed to be inflamed and endure its minimum tensile strength F3 before the proliferation stage 212 begins sometime during day four.

The medicant E configured to prevent inflammation can have a variety of configurations. In general, the medicant E can include an agent configured to inhibit inflammation, e.g., an anti-inflammatory agent. The medicant E can thus be configured to help reduce inflammation at the wound site and, accordingly, help end the inflammation stage 210. Examples of the medicant E include diclofenac.

The medicant E can be administered in a variety of ways. In one example, the medicant E can be administered as a vessel. The vessel can include a coating configured to facilitate release of the medicant E at the appropriate time in the wound healing process, e.g., at a time after release of the MMP-inhibiting medicants D, $D_1$, such as at least 4 days after the injury (4<t), e.g., sometime 7 to 10 days after the injury (7<t<10). Examples of the coating include a copolymer having 90% PGA and 10% PCA and having a high molecular weight, e.g., a higher molecular weight than the coating used for the MMP-inhibiting medicants D, $D_1$ so as to be released thereafter.

The medicant F configured to facilitate tissue growth can have a variety of configurations. In general, the medicant F can include an agent configured to promote tissue growth, e.g., a growth factor. The medicant F can thus be configured to help the tissue rebuild in the proliferation stage 212. Examples of the medicant F include TGF-β.

The medicant F can be administered in a variety of ways. In one example, the medicant F can be administered as a vessel. The vessel can include a coating configured to facilitate release of the medicant F at the appropriate time in the wound healing process, e.g., at a time after release of the anti-inflammatory medicant E, such as at least 5 days after the injury (5<t), e.g., sometime 5 to 10 days after the injury (5<t<10). Examples of the coating include a copolymer having 65% PGA and 35% PCA.

Implementations

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Some aspects of the present disclosure relate to an adjunct releasably retained on a cartridge body of a staple cartridge assembly of a surgical device and configured to be delivered to tissue by deployment of staples in the cartridge body. The adjunct can have at least one first medicant component or medicant configured to be released from the adjunct as a bolus dose substantially immediately upon delivery of the adjunct to tissue a treatment site. The adjunct can also have at least one second medicant component or medicant configured to release from the adjunct such that release of the second medicant to tissue is regulated by the release of the first medicant. In other words, presence of the first medicant and/or other effects provided by the first medicant (e.g., its release from an adjunct or other structure) affect a manner in which the second medicant is released from the adjunct.

The second medicant can be associated with a component of the staple cartridge assembly in a manner that facilitates regulation of its release to tissue by release of the first medicant component. For example, the second medicant can be disposed in the same adjunct as the first component and, in some cases, in the vicinity of a location of the first component in the adjunct. The second medicant can be configured to be released to tissue at a time after the release of the first medicant component.

The first and second medicants can be disposed in an adjunct at locations that facilitate their release therefrom such that the first medicant commences to release before the second medicant and then affects the release of the second medicant. For example, the first medicant can be disposed at a portion of an adjunct along a cut line to be formed, e.g., by a stapler's cutting element. The second medicant can be disposed at one or more portions of the adjunct that are disposed away from the cut line. However, the second medicant can be disposed at the same location as the first medicant while release of the second medicant is still regulated by release of the first medicant. Specifically, release of the first medicant can be triggered by activation of a stapler, whereas release of the second medicant is controlled by the release of the first medicant.

In some implementations, the first medicant can be configured to release as a bolus dose. The second medicant can then release as a time release dose, or in some cases, as a bolus dose. Furthermore, in some implementations, an adjunct can include two or more portions configured such that in some of the portions the second medicant is released as a bolus dose whereas in others it is released as a time-release dose.

In some implementations, the bolus dose of the first medicant can include the second medicant. In such implementations, the second medicant can be disposed within vessels which are disposed in the same location in an adjunct as the first medicant. The first medicant can also be incorporated into vessels such that the adjunct can have both vessels including the first medicant and vessels including the second medicant. The vessels with the second medicant, which can include one or more of second medicants, can be configured to release the second medicant therefrom slower than the vessels carrying the first medicant release the first medicant. In this way, a bolus dose release of the first medicant is followed by release of the second medicant over a longer period of time. In some aspects, the first and second medicants can be the same or they can include the same active agent. In other aspects, the first and second medicants can contain different active agents.

In some implementations, the second medicant can be included in the same vessel (e.g., a pellet, capsule, bead, etc.) as the first medicant. The vessel can be formed from at least one bioabsorbable polymer and the first medicant can be in the form of a layer (e.g., an outer layer) of the vessel. The second medicant can be an active agent and it in the form of one or more inner layers of the vessel such that the second medicant is configured to be released to tissue from the first medicant in the form of the outer layer upon degradation of the bioabsorbable polymer forming the outer layer. In such implementations, release of the second-medicant containing first medicant in the form of multiple vessels from an adjunct (e.g., from one or more reservoirs or other portions thereof) regulates the release of the second medicant from the first medicant. As described above, the vessel can include multiple layers and it can thus have more than one second medicants releasably disposed therein.

Furthermore, an adjust can include a second-medicant containing first medicant in the form or a fiber lattice or a fiber mesh or other structure, as described herein, that releasably retains at least one second medicant containing an active agent. Degradation of at least one bioabsorbable polymer forming such a structure can control release of the at least one second medicant therefrom.

Release of the first medicant from the vessel (e.g., from an outer layer thereof) can allow the second medicant to release from the vessel (e.g., from one or more inner layers thereof) as well. As described above, the vessel can include multiple layers and, in some implementations, release of the first medicant from the vessel can control release of multiple other medicants therefrom.

In some implementations described herein, a bolus dose of the first medicant can be released from a cartridge body. An adjunct releasably retaining the first medicant can be associated with the cartridge body in a number of ways. For example, a staple channel or cavity that holds the staples can also retain at least one medicant therein. The medicants can be included in the adjunct or the adjunct (e.g., in a form of a film) can be used to retain the medicants within one or more staple cavities, in which case the adjunct itself can also include one or more medicants. Deployment of staples can cause the medicant to release from the staple cavity in a manner that can affect release of other medicant(s) from the adjunct.

Figure 45:
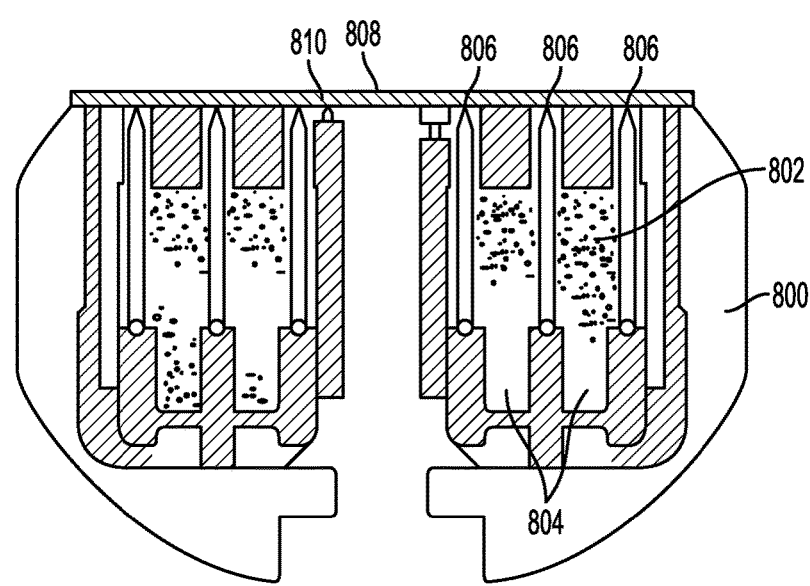
FIG. 45 is a perspective view of an adjunct disposed in a cartridge body.

FIG. 45 illustrates an example of a cartridge body 800 of a staple cartridge of a surgical device having a least one first medicant 802 retained in staple cavities 804 of the cartridge body 800. Each staple cavity 804 has a surgical staple 806 disposed therein. As shown, an adjunct 808 can be configured to releasably retain the at least one first medicant 802 within the staple cavities 804. The adjunct 808 can have at least one second medicant 810 disposed therein, which can be disposed within the adjunct 808 in any suitable way. The first and second medicants 802, 810 can be the same or different medicants.

The adjunct 808 can have a number of different structures and it can be formed from various materials. In the example of FIG. 45, the adjunct 808 can be in the form of a film or other structure. The film can be formed from at least one bioabsorbable polymer having certain elution characteristics (e.g., degradation rate, etc.). An exemplary structure of the adjunct 808 includes a poly-p-dioxanone (PDS) film attached to a woven construct made of oxidized regenerated cellulose (ORC) or other material. The PDS film can be attached to the ORC construct using heat as described, for example, in U.S. patent application Ser. No. 14/667,874 entitled "Malleable Bioabsorbable Polymer Adhesive For Releasably Attaching A Staple Buttress To A Surgical Stapler" filed Mar. 25, 2015, and U.S. Pat. No. 7,601,118 entitled "Minimally Invasive Medical Implant And Insertion Device And Method For Using The Same" and filed Sep. 12, 2007, which are hereby incorporated by reference in their entireties.

Regardless of the specific configuration of an adjunct in accordance with the described subject manner, such as adjunct 808 in FIG. 45, the adjunct can be configured to be penetrated by staples such that content of the adjunct (e.g., at least one second medicant) can be released. Additionally or alternatively, upon delivery of the adjunct to a treatment site, the adjunct can commence to degrade due to moisture and other agents or factors in an external environment at the treatment site.

Figure 46:
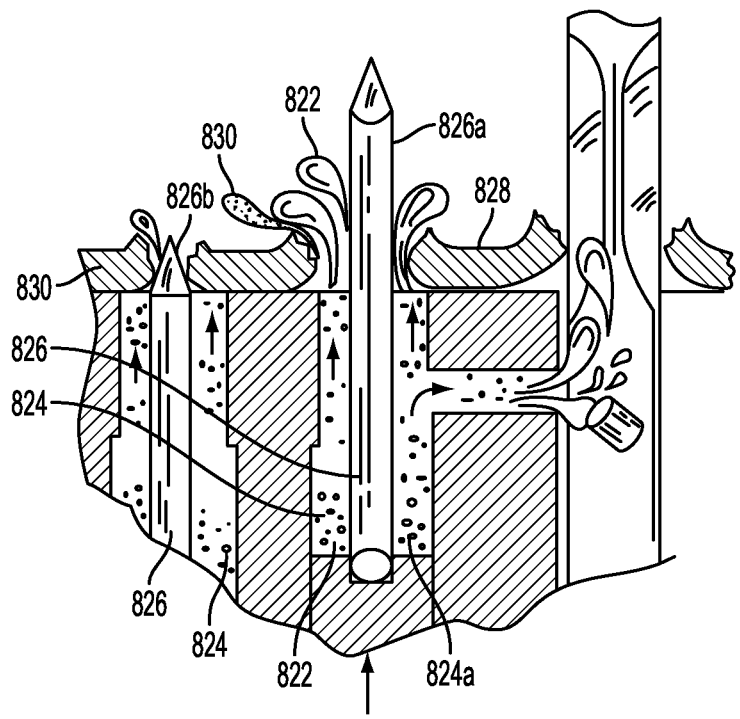
FIG. 46 is a perspective view of a portion of an adjunct disposed in a cartridge body, showing the adjunct penetrated by staples delivered by the cartridge body.

FIG. 46 illustrates an example of a cartridge body 820 similar to cartridge body 800 in FIG. 45. As shown in FIG. 46, the cartridge body 820 has at least one first medicant 822 retained in staple cavities 824 thereof. Each staple cavity 824 has a surgical staple 826 disposed therein, and, in the illustrated example, the surgical staples 826 can be configured to deployed such that they emerge from a tissue-facing surface of the cartridge body 820 at different times. As shown, the cartridge body 820 has an adjunct 828 disposed thereon that is configured to releasably retain the at least one first medicant 822 within the staple cavities 824. The adjunct 828 can be similar to adjunct 808 in FIG. 45 and it can include at least one second medicant 830 releasably disposed therein.

As further shown in FIG. 46, upon deployment of the staples 826, the first medicant 822 can release from the staple cavities 824 as a bolus dose. As mentioned above, in the example of FIG. 46, the surgical staples 826 can penetrate the adjunct 828 disposed on the tissue-facing surface of the cartridge body 820 at different times. Thus, as shown in FIG. 46, a staple 826a can penetrate the adjunct 828 first after which staple 826b penetrates the adjunct 828. As also shown, penetration of the adjunct 828 by the staple 826a causes the first medicant 822 to be released from a respective staple cavity 824a. Also, the second medicant 830 can be released from the adjunct 828, which can be regulated by release of the first medicant 822 from the staple cavity 824a. In aspects in which different staple cavities or rows carry respective different medicants, deployment of the staple 826b after the staple 826a is deployed can cause another medicant to release from the respective staple cavity. The adjunct 828 can include more than one second medicant that can be affected by release of one or more different first medicants from the staple cavities.

In addition, in some implementations, as mentioned above, one or more of the staple cavities can include both the first and second medicant that are releasable from the cavities such that release of the first medicant controls or affects release of the second medicant.

In the examples of FIG. 45 and FIG. 46, a first medicant can be disposed in a cartridge body in a number of different ways. For example, one or more row of staples (linear or circular) in the cartridge body can be dedicated to medicant delivery. Thus, the staple cavities in the row(s) will carry the first medicant 802. Furthermore, in some implementations, one or more staples can be removed from a staple row dedicated to medicant delivery (not shown). In this way, one or more of the staple cavities (e.g., the staple cavities 804 or 824) can retain a dose of the first medicant that can be released when an end effector of the surgical device is deployed. Each of the staple cavities, whether with a staple or having a staple removed, can be associated with one medicant or with a blend of different medicants. Also, each of the staple cavities can be associated with a different medicant. In some aspects, a staple row can be associated with a different medicant such that each staple row in a cartridge body carries a medicant that is different from medicants carried by other staple rows. It should be appreciated that only some of the staple cavities and/or only some of the staple rows in a cartridge body can be associated with one or more medicants.

As mentioned above, an adjunct in accordance with the described techniques can be configured such that release of a first medicant can be triggered by mechanical disruption of a carrier for the first medicant. For example, as described above, the first medicant can be disposed within a coating formed on the staples, and the coating can be disrupted by deformation of the staples. The first medicant can also be disposed within a staple line of the cartridge body, and puncture of a film retaining the first medicant within the staple line can result in release of the first medicant. As another example, the first medicant can be disposed at a cut line to be cut by a tissue cutting instrument of a surgical stapling device.

In some implementations, an adjunct can be configured to incorporate at least one first medicant at a portion thereof to be cut by a tissue cutting instrument, and at least one second medicants at other locations of the adjunct. Examples of such adjuncts are described in U.S. patent application Ser. No. 14/840,659H entitled "Adjunct Material To Provide Heterogeneous Drug Elution" filed on Aug. 31, 2015, which is hereby incorporated by reference in its entirety. The first and second medicants can be released from such an adjunct in various patterns and release of the first medicant can influence release of the second medicant.

An environment created by a first medicant when it is released or as it is being released can affect a rate of release of the second medicant. Staple penetration of an adjunct can result in a bolus dose release of the first medicant whereas a long-term degradation of material forming the adjunct uses release of the second medicant. Examples of components that can release at least one drug upon being cut with a tissue cutting instrument are described in U.S. Pat. App. Publ. No. 2013/0256367 entitled "Tissue Thickness Compensator Comprising A Plurality Of Medicaments" filed on Mar. 28, 2012, which is hereby incorporated by reference in its entirety.

In some implementations, an adjunct can be configured to incorporate at least one first medicant at locations thereof to be punctured by the staples and at least one second medicants at other locations thereof that are between the locations to be punctured by staples. Examples of such adjuncts are described in U.S. patent application Ser. No. 14/840,659 entitled "Adjunct Material To Provide Heterogeneous Drug Elution" filed Aug. 31, 2015.

In some implementations, at least one medicant can be releasably disposed in a dispenser in an elongate shaft of a surgical instrument. Examples of such surgical instruments are described in U.S. Pat. No. 8,905,977 entitled "Surgical Stapling Instrument Having An Electroactive Polymer Actuated Medical Substance Dispenser" filed on Jun. 1, 2005, and U.S. Pat. No. 8,215,531 entitled "Surgical Stapling Instrument Having A Medical Substance Dispenser" filed on Jan. 29, 2010, which are hereby incorporated by reference in their entireties. Movement of as a cutting element, such as knife, can release the at least one medicant contained in the shaft of the surgical instrument. In these implementations, the medicant configured to be release from a shaft of the surgical instrument can be at least one first medicant that affects release of at least one second medicant, as described herein. The at least one second medicant can be releasably disposed in an adjunct that can be releasably retained on a cartridge body of that surgical instrument.

As mentioned above, a staple can be associated with at least one medicant which, in the illustrated implementations, can act as a first medicant affecting release of another medicant. Also, in some cases, the staple leg can include both a first medicant and a second medicant which can be released in dependence from the first one. The at least one medicant can be disposed in an adjunct associated with the staple. As disused above, the adjunct can be in the form of a film, fiber lattice, and/or foam. The staple can carry the adjunct thereon such that at least one medicant disposed in the adjunct can release when the staple is deformed upon staple deployment. One example of such an implementation is adjunct 150 in FIGS. 22 and 23 above. As discussed above, when the staple carrying an adjunct is deformed upon its deployment, an outer surface of the adjunct ruptures and thereby causes at least one retained medicant to release. Also, deformation of the staple can cause the outer surface of the adjunct to deform, which exposes inner coating(s) including at least one medicant (e.g., an anti-microbial agent or antibiotic). As another example, the least one medicant can release from the adjunct associated with a staple due to moisture and other agents to which the adjunct is exposed in tissue of a wound. When a staple is coated with an adjunct in the form of one or more biodegradable layers, the layers can gradually absorb or degrade and thus release at least one medicant under control of the degradation rate. As one example, a non-cross linked coating can swell and become a polymer gel before it begins to break down.

At least one medicant can be directly coated over a staple leg with one or more layers of the medicant coating the staple leg. The staple leg can also be coated with a layer including at least one agent that prevents bio-film formation. The coated medicant may or may not be encapsulated within an outer shell which can be at least one bioabsorbable polymer and/or that can be ruptured in a number of different ways.

Further, staple coating technologies for medicant delivery in accordance with the described techniques can include braiding multiple fibers around a staple wire, as described, for example, in U.S. Pat. No. 8,663,277 entitled "Braided Barbed Suture" filed on Jun. 29, 2005, which is hereby incorporated by reference in its entirety. The fibers can be disposed over the staple wire before the staple is formed and loaded into a cartridge. One or more of the fibers can contain medicants, as discussed herein. Examples of staples carrying multiple layers at least one of which retains one or more medicants are discussed in U.S. patent application Ser. No. 14/841,139 entitled "Adjunct Material To Provide Controlled Drug Elution" filed on Aug. 31, 2015, which is hereby incorporated by reference in its entirety.

Figure 47:
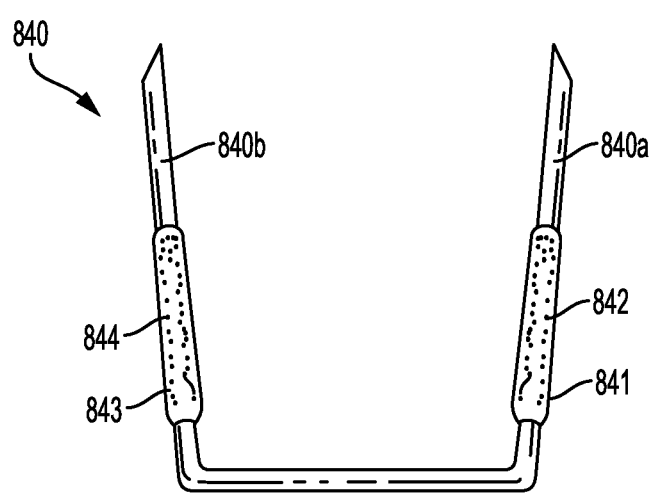
FIG. 47 is a perspective view of a staple with medicants.

FIG. 47 illustrates an exemplary implementation of a surgical staple 840 that can be used in conjunction with the described subject manner. As illustrated, the staple 840 has first and second medicants 842, 844 disposed on legs 840a, 840b thereof. The first and second medicants 842, 844 can be the same or different medicants. In the example illustrated, the first and second medicants 842, 844 can be disposed within respective adjuncts 841, 842 formed of at least one bioabsorbable polymer and disposed over the staple legs 840a, 840b. As the polymer disintegrates, the medicants can be released therefrom. The adjunct can be configured to be disrupted and thereby release its content when strain is applied thereto, as discussed above. However, it should be appreciated that the medicants 842, 844 can be associated with the staple legs in a number of different ways, including ways that differ among the legs. For example, the medicants 842, 844 can be coated over at least a portion of the staple legs in their pure form or as incorporated into at least one bioabsorbable polymer, at least partially impregnated into the portion(s) of the staple legs, or otherwise releasably associated with the staple legs 840a, 840b.

Figure 48:
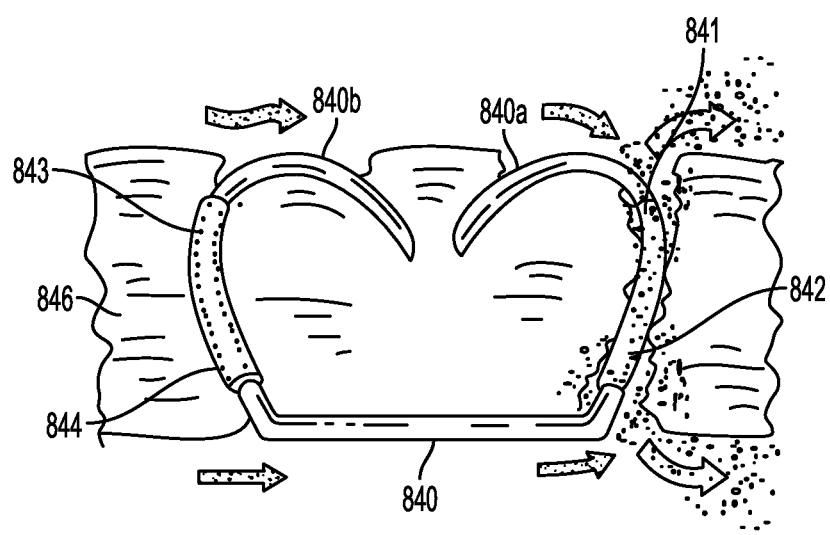
FIG. 48 is a cross-sectional view of tissue with the staple of FIG. 47 inserted therethrough.

When the staple 840 is delivered to a tissue 846 such that the legs 840a, 840b bend towards each other, as shown in FIG. 48, the first and second medicants 842, 844 can release from the adjuncts 841, 843 coated over the staple 840 and can be delivered to the tissue 846. In this exemplary implementation, as shown in FIG. 47, the first medicant 842 can be configured to release from the adjunct 841 on the leg 840a before the second medicant 844 is released from the adjunct 843 on the leg 840b. As mentioned above, degradation of at least one bioabsorbable polymer forming the adjunct 841 can cause the first medicant 842 to escape the adjunct. Additionally or alternatively, as mentioned above, the first medicant 842 can be released from the adjunct 841 due to deformation of the leg 840a and resulting strain applied to the adjunct 841. The second medicant 844 can subsequently be released from the adjunct 843 in the same or other manners. In some implementations, the first and second medicants 842, 844 can be configured to release from the staple 840 substantially simultaneously.

Regardless of the specific way in which the first and second medicants 842, 844, which can be the same medicant(s), are associated with the staple 840 and are releasable therefrom, these medicants can release therefrom when the staple 840 is delivered to the tissue 846. Furthermore, although not shown in FIG. 48, in addition to carrying the medicants 842, 844, the staple 840 can be used to deliver an adjunct to the tissue 846 which can be disposed over a cartridge body. Such adjunct can releasably retain at least one third medicant therein. Release of one or both of the medicants 842, 844 can affect release of the at least one third medicant in accordance with the described techniques.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A staple cartridge assembly for use with a surgical stapler, comprising:
 a cartridge body having a plurality of staple cavities, each staple cavity having a surgical staple disposed therein;

a bioabsorbable adjunct material releasably retained on the cartridge body and configured to be delivered to tissue by deployment of the staples in the cartridge body; and a first medicant component associated with a component of the staple cartridge assembly in a manner in which the first medicant component is released as a bolus dose substantially immediately upon delivery of the adjunct material to tissue, such that the first medicant component is released in its entirety from the component of the staple cartridge assembly; and a second medicant component associated with a component of the staple cartridge assembly in a manner such that release of the second medicant component to tissue is regulated by the release of the first medicant component.

2. The cartridge assembly of claim 1, wherein the second medicant component is configured to be released to tissue at a time after the release of the first medicant component.

3. The cartridge assembly of claim 1, wherein the second medicant component is configured to be released to tissue over a period of time commencing at a time following release of the first medicant component.

4. The cartridge assembly of claim 3, wherein the second medicant component is a first active agent disposed within a bioabsorbable polymer that is configured to be released from the first medicant component upon release of the first medicant component, the first active agent being configured to be released to tissue upon degradation of the bioabsorbable polymer.

5. The cartridge assembly of claim 4, wherein the first and second medicant components contain the same active agent.

6. The cartridge assembly of claim 4, wherein the first medicant component is a second active agent that is different than the first active agent.

7. The cartridge assembly of claim 1, wherein the release of the first medicant component is configured to be triggered by mechanical disruption of a carrier for the first medicant component.

8. The cartridge assembly of claim 7, wherein the first medicant component is disposed within a coating formed on the staples, and the mechanical disruption is deformation of the staples.

9. The cartridge assembly of claim 7, wherein the first medicant component is disposed within a staple line of the cartridge body, and the mechanical disruption is puncture of a film retaining the first medicant component within the staple line.

10. The cartridge assembly of claim 1, wherein the second medicant component is disposed within the adjunct material.

11. An end effector for a surgical instrument, comprising:
a first jaw having a cartridge body removably attached thereto, the cartridge body having on a tissue-facing surface thereof a plurality of staple cavities configured to seat staples therein;

a second jaw having an anvil with a plurality of staple forming cavities formed on a tissue-facing surface thereof, wherein at least one of the first and second jaws is movable relative to the other;

a biocompatible adjunct material releasably retained on at least one of the tissue-facing surfaces of the cartridge body first and the anvil and configured to be delivered to tissue by deployment of the staples in the cartridge body;

a first medicant component associated with a component of the staple cartridge assembly in a manner in which the first medicant component is released as a bolus dose substantially immediately upon delivery of the adjunct material to tissue such that the first medicant component is released in its entirety from the component of the staple cartridge assembly; and a second medicant component associated with a component of the staple cartridge assembly in a manner such that release of the second medicant component to tissue is regulated by the release of the first medicant component.

12. The end effector of claim 11, wherein the second medicant component is configured to be released to tissue at a time after the release of the first medicant component.

13. The end effector of claim 11, wherein the second medicant component is configured to be released to tissue over a period of time commencing at a time following release of the first medicant component.

14. The end effector of claim 13, wherein the second medicant component is a first active agent disposed within a bioabsorbable polymer that is configured to be released from the first medicant component upon release of the first medicant component, the first active agent being configured to be released to tissue upon degradation of the bioabsorbable polymer.

15. The end effector of claim 14, wherein the first and second medicant components contain the same active agent.

16. The end effector of claim 14, wherein the first medicant component is a second active agent that is different than the first active agent.

17. The end effector of claim 11, wherein the release of the first medicant component is configured to be triggered by mechanical disruption of a carrier for the first medicant component.

18. The end effector of claim 17, wherein the first medicant component is disposed within a coating formed on the staples, and the mechanical disruption is deformation of the staples.

19. The end effector of claim 17, wherein the first medicant component is disposed within a staple line of the cartridge body, and the mechanical disruption is puncture of a film retaining the first medicant component within the staple line.

20. The end effector of claim 11, wherein the second medicant component is disposed within the adjunct material.

* * * * *